US006306805B1

(12) United States Patent
Bratescu et al.

(10) Patent No.: US 6,306,805 B1
(45) Date of Patent: Oct. 23, 2001

(54) SHAMPOO AND BODY WASH COMPOSITION COMPRISING TERNARY SURFACTANT BLENDS OF CATIONIC, ANIONIC, AND BRIDGING SURFACTANTS AND METHODS OF PREPARING SAME

(75) Inventors: Daniela T. Bratescu, Glenview; Randy Bernhardt; Cathie Sporer, both of Lindenhurst; Sandy Lyons, Glencoe; Jeff Nelson, Lake Bluff, all of IL (US); Rita Bezdicek, Shanghai (CN)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 09/663,463

(22) Filed: Sep. 15, 2000

(51) Int. Cl.$^7$ ............................... C11D 1/86; C11D 1/90; C11D 1/62; C11D 1/12; C11D 1/75

(52) U.S. Cl. .................. 510/123; 510/119; 510/124; 510/125; 510/426; 510/427; 510/428; 510/429; 510/433; 510/503; 510/504

(58) Field of Search ....................... 510/119, 123, 510/124, 125, 426, 427, 428, 429, 433, 503, 504

(56) References Cited

U.S. PATENT DOCUMENTS

| | | | |
|---|---|---|---|
| 3,929,678 | 12/1975 | Laughlin et al. | 252/526 |
| 4,744,977 | 5/1988 | Hensen et al. | 424/70 |
| 4,913,828 | 4/1990 | Caswell et al. | 252/88 |
| 4,931,216 | 6/1990 | Igarashi et al. | 252/547 |
| 4,978,526 | 12/1990 | Gesslein et al. | 424/70 |
| 5,071,594 | * 12/1991 | Borland et al. | 252/528 |
| 5,145,607 | 9/1992 | Rich | 252/547 |
| 5,441,541 | 8/1995 | Mehreteab et al. | 8/137 |
| 5,607,980 | 3/1997 | McAtee et al. | 514/476 |
| 5,622,925 | 4/1997 | de Buzzaccarini et al. | 510/329 |
| 5,747,436 | 5/1998 | Patel et al. | 510/124 |
| 5,759,208 | * 6/1998 | Zhen et al. | 8/137 |
| 5,939,059 | 8/1999 | Franklin et al. | 424/70.19 |
| 5,997,854 | 12/1999 | von Mallek | 424/70.19 |
| 6,007,802 | 12/1999 | Coffindaffer et al. | 424/70.19 |

FOREIGN PATENT DOCUMENTS

| | | |
|---|---|---|
| 62126113 | 6/1987 | (JP) . |
| 63156713 | 6/1988 | (JP) . |
| 6293620 | 10/1994 | (JP) . |
| 2558704 | 9/1996 | (JP) . |
| WO 97/03164 | 1/1997 | (WO) . |
| WO 97/12022 | 4/1997 | (WO) . |
| WO 98/29094 | 7/1998 | (WO) . |
| 98/29094 | * 7/1998 | (WO) . |
| WO 99/58106 | 11/1999 | (WO) . |

* cited by examiner

Primary Examiner—Yogendra N. Gupta
Assistant Examiner—Charles Boyer
(74) Attorney, Agent, or Firm—McDonnell Boehnen Hulbert & Berghoff

(57) ABSTRACT

The present invention relates to surfactant compositions comprising a mixture of at least one cationic surfactant, at least one anionic surfactant, preferably a sulfonated methyl ester and/or a sulfonated fatty acid, and at least one "bridging surfactant" selected from semi-polar nonionic, ethoxylated alkanolamide, and amphoteric/zwitterionic surfactants, and mixtures thereof. More specifically, the invention relates to stable, synergistic mixtures of cationic, anionic, and bridging surfactants that are useful primarily as shampoos and/or body washes. The instant invention further provides both a method for preparing the inventive surfactant compositions, i.e., shampoos, and a method of treating hair with the shampoo compositions. When applied to hair or skin, the surfactant shampoo compositions of the instant invention generally provide for cleaning, conditioning, bodifying, and/or moisturization of the hair or skin.

50 Claims, No Drawings

SHAMPOO AND BODY WASH COMPOSITION COMPRISING TERNARY SURFACTANT BLENDS OF CATIONIC, ANIONIC, AND BRIDGING SURFACTANTS AND METHODS OF PREPARING SAME

FIELD OF THE INVENTION

The present invention relates to surfactant compositions comprising a mixture of at least one cationic surfactant, at least one anionic surfactant, preferably a sulfonated methyl ester and/or a sulfonated fatty acid, and at least one "bridging surfactant" selected from semi-polar nonionic, ethoxylated alkanolamide, and amphoteric/zwitterionic surfactants, and mixtures thereof. More specifically, the invention relates to stable, synergistic mixtures of cationic, anionic, and bridging surfactants that are useful primarily as shampoos and/or body washes. The instant invention further provides both a method for preparing the inventive surfactant compositions, i.e., shampoos, and a methods of treating hair with the shampoo compositions. When applied to hair, the surfactant shampoo compositions of the instant invention generally provide for cleaning, conditioning, bodifying, and/or moisturization of the hair.

BACKGROUND OF THE INVENTION

The process of hair care is multifaceted and generally involves washing, conditioning, and styling the hair. The desirable results of the hair care process include a persistent look and feel of clean hair between washings, ease of combing, absence of static electricity, manageability, soft feel and shine. A limited number of hair care products are available which clean as well as condition the hair by the use of one product, i.e., a two-in-one conditioning shampoo. Certain two-in-one conditioning shampoos typically contain water, anionic surfactants, foam stabilizers, insoluble non-volatile silicone conditioning agents and silicone suspending agents. Other such products contain cationic conditioning agents in place of silicone. However, all of these singular shampoo products and/or two-in-one products have various limitations. These limitations are well known in the art. Other hair care products are available which simultaneously clean, condition and control dandruff, i.e., a 3-in-1 anti-dandruff shampoo. These too have well known limitations.

Since known two- and three-in-one hair care products have various limitations, a need exists for surfactant based shampoo compositions which are capable of delivering cleaning, foaming and/or conditioning properties to the hair, with limited or no build up of the compositions on the hair after multiple application. It is desired that new hair care compositions provide comparable or superior cleaning, foaming and/or conditioning properties to the hair, as compared to prior art hair care compositions. Further, a need exists for compositions with the above-described properties which are efficacious on fine, long, or chemically damaged hair.

General detergent anionic-cationic surfactant mixtures are well known to the art. See generally, U.S. Pat. Nos. 5,441,541, 5,472,455, 5,204,010, 4,790,856, 4,298,480, 3,730,912 (all to The Colgate-Palmolive Company), 5,622,925, 5,607, 980, 5,565,145, 4,913,828, 4,659,802, 4,436,653, 4,338,204, 4,333,862, 4,132,680 (all to The Procter & Gamble Co.); also see WO 97/03164, WO 97/12022 and WO 96/37591 (all to The Procter & Gamble Co.), and WO 97/28238 and WO 97/15647 (both to Reckitt & Colman, Inc.). See also, U.S. Pat. Nos. 5,610,187 and 4,247,538 (both to Witco Corp.), 5,344,949 (to Th. Goldschmidt AG), 5,332,854 and 5,324, 862 (both to Dai-Ichi Kogoyo Seiyaku Co., Ltd.), 4,273,760 (to National Starch and Chemical), and 4,264,457 (to DeSoto, Inc.). Mixed surfactant systems have also been disclosed in "Mixed Surfactant Systems", ACS Symposium Series 501, P. M. Holland and D. N. Rubingh (Jun. 17–19, 1991).

Additionally, there have been many studies and symposia on mixed surfactant systems. See, for example, Scamehorn, J. F., ed., "Phenomena in Mixed Surfactant Systems", ACS Symposium Series 311, Washington, D.C. (1986). The effects of alkyl groups and oxyethylene groups in nonionic surfactants on the surface tension of anionic-nonionic systems have been described. See Abe et al., J. Colloid Interface Sci., 107, p. 503 (1985); Ogino et al., J. Colloid Interface Sci., 107, p. 509 (1985); and Rosen et al., J. Colloid Interface Sci., 95, 443 (1983). Interaction between betaines and cationic surfactants has also been studied. See Zhu et al., J. Colloid Interface Sci., 108, 423 (1985).

Mixed surfactant systems have shown synergistic improvements in surfactant properties compared to the properties of their individual surfactant components. Synergism increases with the degree of charge difference. Thus, the greatest synergistic surfactant property improvements are realized when mixing anionic and cationic surfactants. See Rosen et al. in "Phenomena in Mixed Surfactant Systems" (Scamehorn, J. F., ed.), ACS Symposium Series 311, Washington, D.C. (1986), pp. 144–162; Zhao et al. in "Phenomena in Mixed Surfactant Systems" (Scamehorn, J. F., ed.) ACS Symposium Series 311, Washington, D.C. (1986) pp. 184–198.

In detergent applications, although in principle any surfactant is suitable, in practice only anionic and nonionic surfactants typically are used. Cationic surfactants, especially quaternary ammonium salts, can decrease detergency and enhance soil redeposition when used in heavy-duty liquid detergents. Consequently, there is a general notion that anionic and cationic surfactants cannot be used in the same formula without loss of efficacy. Similar worries regarding potential loss of efficacy exist when contemplating use of cationic surfactants in hair and skin conditioning applications. Thus, anionic-cationic surfactant mixtures have been used only sparingly in the production of consumer cleaning products and personal care products.

Studies on anionic-cationic systems are recent and few compared to studies on other mixed surfactant systems. However, strong synergism has been exhibited by these systems. Surface activity properties, particularly the critical micelle concentration (cmc), surface tension, and micro-emulsion behavior (Bourrel et al., Tenside Detergents, 21, 311 (1984)), were the most studied properties. For example, the surface activities of mixed aqueous solutions of sodium dihexylsulfosuccinate with dioctyl(hydroxyethyl) methylammonium chloride and sodium dihexylsulfosuccinate with octyl(hydroxyethyl)dimethylammonium chloride were much higher than those of the single surfactants. See Zao, G., Huoxue Xuebo, 43, 705 (1985) (Ch. Chem. Abstracts 103:184033n). The strong synergistic effect on surface pressure for mixed solutions of cationic and anionic surfactants has been studied quantitatively. When dilute solutions of sodium dodecylsulfate and dodecyltrimethy-lammonium bromide were mixed, tile surface pressure increased by more than 40 mN/m. Also, the cmc and the minimum surface tension were lower for the mixture than for either the anionic or cationic surfactants alone (Lucassen-Reynders et al., J. Colloid Interface Sci., 81, p. 150 (1981)).

However, mixed anionic-cationic mixtures also have shown antagonistic effects relative to the properties of the individual surfactant components. See Chobanu et al., Izv. Akad. Nauk. Mold. SSR, Ser. Biol. Khim. Nauk., 5, p. 66 (1982). Unlike other mixed surfactant systems, most anionic-cationic surfactant mixtures studied are insoluble or only slightly soluble in water. Hence, practical use of anionic-cationic surfactant mixtures has been very limited in areas where a relatively high concentration of surfactants is needed (see U.S. Pat. No. 5,472,455, to Mehreteab, issued Dec. 5, 1995). Thus, there is a need for soluble anionic-cationic surfactant mixtures.

At present, very few anionic-cationic surfactant mixtures have been found which produce clear solution phases over a wide concentration range at equimolar composition. See generally, Khan, A.; Marques, E.; *Spec. Surfactants* 1997, 37–80, edited by Robb, I. D. Blackie. Typically, anionic-cationic surfactant mixtures are present as microemulsions, rather than as clear, homogeneous solutions. Usually, the anionic and/or cationic surfactant must be alkoxylated to even maintain such a microemulsion.

Because the probability of synergism between surfactants increases with the strength of interaction, the greatest probability of synergism with anionic surfactants exists in anionic-cationic or anionic-zwiterionic mixtures. See generally, *Surfactant and Interfacial Phenomena*; Rosen, M.; John Wiley & Sons, Inc. 1989 p. 402. Surfactant performance is gauged by the so-called β value, which is a negative number indicating how much less a system's actual surface tension is compared to its calculated surface tension. Surfactant mixtures exhibiting larger deviations between calculated and actual surface tension perform better; thus, surfactant performance increases with progressively more negative β values. However, with respect to anionic-cationic mixtures, the variations in surfactant type and size that produce progressively more negative β values unfortunately are accompanied by decreasing solubility. Hence anionic-cationic synergism is limited by the formation of an insoluble salt, which typically occurs when the combined number of carbon atoms in the chains of both surfactants totals more than about twenty. See generally, Lomax, E; *Specialty Chemicals* 1993, v 13 n 4 p 223–227). A method for enhancing the solubility of anionic-cationic surfactant mixtures is therefore needed to allow achieving maximum negative β values.

In addition to detergent mixed surfactant systems, shampoo compositions comprising anionic-cationic surfactant mixtures are also relatively well known. U.S. Pat. No. 6,007,802 (to Procter & Gamble) discloses a conditioning shampoo composition with excellent cleaning performance and improved levels of conditioning while minimizing any adverse effect associated with build-up; the disclosed compositions general comprise an ethoxylated alkyl sulfate, amphoteric surfactant, insoluble, dispersed conditioning agent (nonionic, cationic silicone), synthetic esters, and cellulosic cationic polymers. U.S. Pat. No. 5,939,059 (to Akzo Nobel) discloses a 2-in-1 conditioning shampoo comprising an anionic surfactant (alkyl sulfate or ether sulfate) and ester quats, with optional amide. U.S. Pat. No. 5,747, 436 (to Colgate Palmolive) discloses a low static conditioning shampoo comprising an anionic and an amphoteric surfactant, complex acid:amine (1:1 mole ratio) and polyquaternary compound. U.S. Pat. No. 5,607,980 (to Procter & Gamble) discloses topical compositions having improved skin feel comprising an anionic surfactant (alkyl sulfate, ether sulfate, isethionate), a cationic surfactant and an amphoteric surfactant. U.S. Pat. No. 5,997,854 (to Henkel) discloses a conditioning shampoo formulation comprising a quaternary ammonium component, an emulsifier, an amphoteric, an alkyl polyglycoside surfactant. U.S. Pat. No. 5,145,607 (to Takasago International Corporation) discloses an optically clear conditioning shampoo comprising anionic (alkyl sulfate or alkyl ether sulfate) and cationic surfactants. U.S. Pat. No. 4,931,216 (to Kao Corporation) discloses detergent compositions comprising an anionic or amphoteric surface active agents and a branched quaternary ammonium salt. U.S. Pat. No. 4,744,977 (to Henkel) discloses quaternary ammonium compound hair conditioners in combination with an anionic surfactant. U.S. Pat. No. 5,661, 189 (to Unilever) discloses mixtures of anionic, cationic, amphoteric, nonionic, zwitterionic surfactants, along with benefit agents, thickening agents an small amounts of soap.

Additionally, WO 98/29094 (to Procter & Gamble) discloses conditioning shampoo compositions comprising a polyhydrophilic anionic surfactant, a cationic surfactant, and a polyvalent cation, along with optional amphoteric surfactants. EP0937452A2 (to Goldwell) discloses hair conditioning agents containing esterquats and anionic compounds. JP-62126113 (to Lion) discloses shampoos containing quaternary ammonium salts and anionic surfactants, such as alkyl sulfate, ether sulfate and olefin sulfonate. JP-63156713 (to Kokai Tokkyo Koko) discloses shampoos containing cationic surfactants, amphoteric sulfonates, alpha olefin sulfonates and various other sulfates. JP-6293620 (to Kokai Tokkyo Koko) discloses shampoos compositions containing anionic (ether sulfate, sulfosuccinate), amphoteric and cationic surfactants. JP-63313711 (to Kokai Tokkyo Koko) discloses shampoo compositions containing alpha olefin sulfonates and/or sulfate salts, quaternary ammonium salts and amidoalkyl betaine surfactants.

For other mixed surfactant systems for use in shampoo formulations, see generally, U.S. Pat. Nos. 4,913,828 (to Procter & Gamble); 5,441,541 (to Colgate-Palmolive); 4,978,526 (to Inolex); 3,929,678 (to Procter & Gamble); and 5,622,925 (to Colgate-Palmolive). Additionally, see WO 99/58106 (to Witco); JP 2558704 (to Lion); WO 97/12022 (to Procter & Gamble); and WO 97/03164 (to Procter & Gamble).

Generally and without being bound by any particular theory, the general benefits associated with solubilized anionic/cationic systems are best explained by the theory that surfactant molecules of opposite charge pack more closely to each other in micelles due to the absence of any electrostatic repulsion. This close packing in turn leads to more efficient soil removal. See generally, Lomax, E., supra. Prior art attempts to solubilize anionic-cationic surfactant systems include the use of organic solvents, such as butanol or ethanol. Also, reported is the use of nonionic surfactants as solubilizing agents or incorporation of alkoxy groups into the anionic and/or cationic surfactants. Unfortunately, addition of organic solvents presents a fire hazard and/or possible skin sensitization and is generally unacceptable in shampoo compositions. Additionally, addition of nonionic components tends to keep the anionic and cationic surfactant molecules further apart, decreasing the overall efficacy of the system. Once again without being bound by any particular theory, the oppositely charged surfactant molecules are kept further apart due to stearic hindrance and because of the osmotic effects which force water molecules between the two surfactant molecules, diminishing the beneficial effect of closer packing.

Thus, in addition to the previous mentioned needs, there is a need for anionic-cationic surfactant blends that are efficacious in shampoo formulations, readily soluble in water at a variety of concentrations, easy to handle, and safe to handle. Accordingly, it has been surprisingly discovered that soluble and substantially soluble shampoo compositions comprising mixtures of anionic and cationic surfactants can be prepared without the use of flammable organic solvents. The shampoo compositions of the present invention are anionic-cationic-bridging surfactant blends which generally form clear solutions at a variety of concentrations in water.

SUMMARY OF THE INVENTION

The present invention provides surfactant compositions which are particularly useful for preparing a variety of finished consumer cleaning products, including for example multi-functional shampoos and body washes. The present invention accordingly provides surfactant shampoo (or body wash) compositions which impart cleaning, foaming and/or conditioning properties to the hair. Although these products are the focus of the invention, the surfactant compositions disclosed herein may be used to prepare finished liquid dish detergents, laundry detergents, automatic dishwasher detergents, hand soaps, laundry bars, personal cleansing bars, multi-purpose cleaners and textile treatment compositions. Surfactant blends of the present invention also may be optionally employed as surfactants in agricultural and pesticide applications. Additionally, the surfactant blends may be utilized in antimicrobial detergent formulations (e.g., antimicrobial hard surface cleaners, hand soaps, shampoos, and dish detergents), soft-terg delivery systems and pre-spotter compositions. Surfactant blends of the present invention may be prepared in various concentrations and exhibit a wide range of rheological behavior. The surfactant blends display excellent detergent, cleaning and conditioning properties.

One aspect of the present invention relates to surfactant complexes comprising at least one cationic surfactant, at least one anionic surfactant which is preferably selected from the group consisting of an alpha sulfonated alkyl ester, a sulfonated fatty acid, or a mixture thereof, and at least one "bridging surfactant" selected from nonionic, semi-polar nonionic, and amphoteric/zwitterionic surfactants, and mixtures thereof. These complexes are useful in a variety of end use surfactant applications and as rheology modifiers in a wide variety of surfactant compositions.

The present invention furnishes substantially water-soluble ternary surfactant blends which provide improved performance, such as for example, increased surface tension reduction, improved wetting times, and increased foam volume and stability, to detergent and personal care surfactant formulations. Additionally, ternary blends of the present invention provide for improved greasy, oily soil removal from surfaces and textiles. The blends are also capable of providing conditioning properties to skin, hair and textiles.

Surprisingly, it has been discovered that complexes of anionic and cationic surfactants can be utilized in combination with a bridging surfactant to produce ternary surfactant blends which allow the anionic-cationic complex to remain relatively soluble in aqueous solutions, and at a variety of concentrations, without the use of solubilizing organic solvents or insertion of alkoxy chains into the anionic or cationic surfactants. The surfactant blends when diluted to a concentration of about 0.1 percent by weight in water generally form a clear aqueous solution substantially free of precipitates. As used herein, the term "flowable" means fluid under gravity at ambient conditions (about 1 atmosphere of pressure at about 25° C.) without application of mechanical energy. As used herein, the term "clear" means allowing at least 50% transmittance measured spectrophotometrically at 700 nanometers using water as the standard for 100% transmittance. Typically, the ternary surfactant blend comprises (a) at least one cationic surfactant, (b) at least one anionic surfactant, and (c) at least one bridging surfactant. In many cases the molar ratio of (a):(b):(c) is generally about 1:1:1. However, to optimize performance, the molar ratio of the components can vary as conditions may dictate.

In one aspect, the invention provides a surfactant composition, which is suitable for use in shampoo and body wash finished formulations, comprising:

(a) from about 0.05% to about 5% by weight based on the total weight of the composition of a cationic surfactant which is a quaternary ammonium compound of the formula:

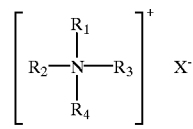

where
$R_1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and (b) an anionic surfactant comprising
i) from about 3% to about 22% by weight based on the total weight of the composition of an alpha sulfonated alkyl ester of the formula

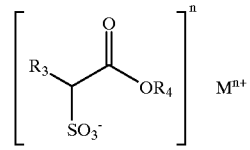

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 11% by weight based on the total weight of the composition of a sulfonated fatty acid of the formula

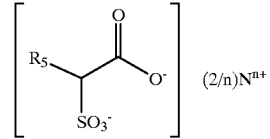

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;

wherein the total concentration of combined cationic, anionic, and bridging surfactants is from about 3% to about 40% by weight based on the total weight of the composition.

In another aspect, the invention provides a surfactant composition, which is suitable for use in shampoo and body wash finished formulations, comprising:

(a) from about 0.05% to about 5% by weight based on the total weight of the composition of a cationic surfactant which is a quaternary ammonium compound of the formula:

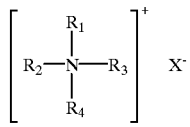

where $R^1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and (b) an anionic surfactant comprising i) from about 3% to about 25% by weight based on the total weight of the composition of an alpha sulfonated alkyl ester of the formula

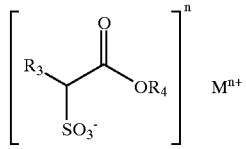

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 15% by weight based on the total weight of the composition of a sulfonated fatty acid of the formula

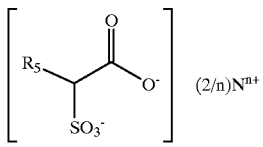

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;

wherein the total concentration of combined cationic, anionic, and bridging surfactants is from about 3% to about 40% by weight based on the total weight of the composition.

In another aspect, the invention provides a method of preparing a surfactant composition comprising combining:

(a) from about 0.05% to about 5% by weight based on the total weight of the composition of a cationic surfactant which is a quaternary ammonium compound of the formula:

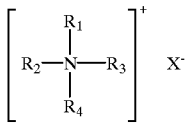

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and (b) an anionic surfactant comprising i) from about 3% to about 22% by weight based on the total weight of the composition of an alpha sulfonated alkyl ester of the formula

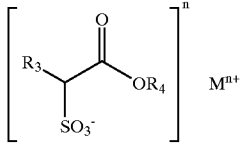

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 11% by weight based on the total weight of the composition of a sulfonated fatty acid of the formula

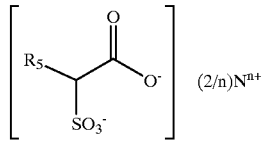

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or mixtures thereof; and (d) water;

wherein the total concentration of combined cationic, anionic, and bridging surfactants is from about 3% to about 40% by weight based on the total weight of the composition.

In still another aspect, the invention provides a method for preparing a surfactant composition comprising combining:

(a) from about 0.05% to about 5% by weight based on the total weight of the composition of a cationic surfactant which is a quaternary ammonium compound of the formula:

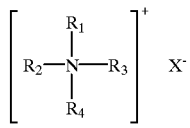

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and (b) an anionic surfactant comprising i) from about 3% to about 25% by weight based on the total weight of the composition of an alpha sulfonated alkyl ester of the formula

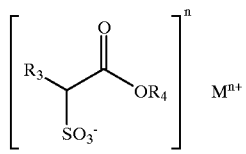

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 15% by weight based on the total weight of the composition of a sulfonated fatty acid of the formula

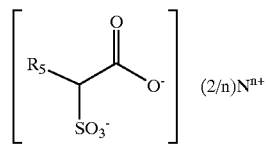

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;

wherein the total concentration of combined cationic, anionic, and bridging surfactants is from about 3% to about 40% by weight based on the total weight of the composition.

The instant invention further provides a method of cleaning and/or conditioning hair or skin comprising (a) optionally wetting the skin or hair;

(b) applying to the skin or hair an effective cleaning and/or conditioning amount of a surfactant composition comprising i) from about 0.05% to about 5% by weight based on the total weight of the composition of a cationic surfactant which is a quaternary ammonium compound of the formula:

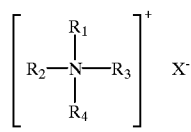

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and ii) an anionic surfactant comprising a) from about 3% to about 22% by weight based on the total weight of the composition of an alpha sulfonated alkyl ester of the formula

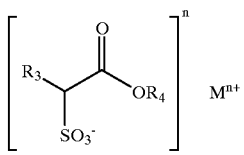

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and b) from about 0.01% to about 11% by weight based on the total weight of the composition of a sulfonated fatty acid of the formula

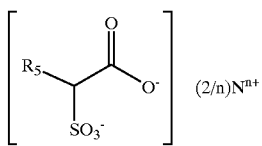

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of a) to b) is from about 10:1 to about 0.5:1; and iii) from about 0.01% to about 15% by weight based on the total weight of the composition a bridging surfactant selected from the group consisting of amine oxides, ethoxamides, and betaines or a mixture thereof; and iv) water;

wherein the total concentration of combined cationic, anionic, and bridging surfactants is from about 3% to about 40% by weight based on the total weight of the composition; and (c) optionally rising the surfactant composition from the skin or hair with water.

The invention also provides a method of cleaning and/or conditioning hair or skin comprising (a) optionally wetting the skin or hair;

(b) applying to the skin or hair an effective cleaning and/or conditioning amount of a surfactant composition comprising i) from about 0.05% to about 5% by weight based on the total weight of the composition of a cationic surfactant which is a quaternary ammonium compound of the formula:

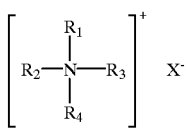

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and ii) an anionic surfactant comprising a) from about 3% to about 25% by weight based on the total weight of the composition of an alpha sulfonated alkyl ester of the formula

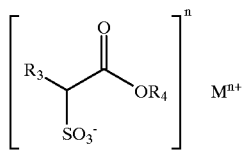

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and b) from about 0.01% to about 15% by weight based on the total weight of the composition of a sulfonated fatty acid of the formula

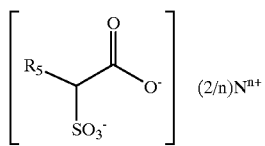

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of a) to b) is from about 10:1 to about 0.5:1; and iii) from about 0.01% to about 15% by weight based on the total weight of the composition a bridging surfactant selected from the group consisting of amine oxides, ethoxamides, and betaines or a mixture thereof; and iv) water;

wherein the total concentration of combined cationic, anionic, and bridging surfactants is from about 3% to about 40% by weight based on the total weight of the composition; and (c) optionally rising the surfactant composition from the skin or hair with water.

The invention provides for a method for increasing the viscosity of alpha sulfonated alkyl ester based surfactant composition, where by incorporation of cationic and bridging surfactants to such a composition greatly increase the viscosity of the composition, as compared to the composition in their absence.

The invention provides surfactant blends comprising a synergistic mixture of anionic, cationic and bridging surfactants that are generally water soluble without the use of organic solvents or insertion of alkoxy chains into either the anionic or cationic surfactant.

The invention further provides surfactant blends exhibiting excellent surfactant properties comprising a synergistic mixture of anionic and cationic surfactants that are generally flowable at concentrations a variety of concentrations and, when diluted to a concentration of about 0.1 percent by weight in water, generally form clear aqueous solutions substantially free of precipitates.

The surfactant compositions of the present invention optionally contain from about 0.001 percent to about 10 percent of optional ingredients selected from the group comprising anti-dandruff agents, fragrance oils, perfumes, coloring agents, dyes, sequestering agents, preservatives, pearlescent/suspending agents, thickener, viscosity modifiers, pH adjusting agents, gelling agents, opacifying agents, foam stabilizing auxiliary surfactants, silicone oils, non-volatile/nonionic silicone conditioning agents, vitamins, protein, sunscreen agents and mixtures thereof.

These and other aspects and advantages, as well as the scope, nature, and utilization of the claimed invention will become apparent to those skilled in the art from the following detailed description and claims.

DETAILED DESCRIPTION OF THE INVENTION

Cationic and anionic surfactants form complexes that are generally insoluble because the charged heads (anionic or cationic) responsible for water solubility are neutralized during complexation. Surprisingly, it has been found that if the cationic surfactant and anionic surfactant are combined with a bridging surfactant to form a ternary blend, a substantially water-soluble system is produced. In ternary surfactant blends of the invention, the use of additional hydrophilic groups (such as ethylene oxide groups or additional charge that remains un-neutralized during complexation) on the anionic or cationic surfactant is not necessary to produce a water-soluble complex. Water solubility in diluted form is assured if an appropriate bridging surfactant is utilized in combination with the anionic and cationic surfactant.

The present invention provides ternary blends of cationic, anionic and bridging surfactants wherein anionic/cationic complexes are formed. While not intending to be limited by a particular theory, it is believed that the quaternary ammonium agent (a cationic surfactant) and anionic surfactants typically form ion pair complexes in aqueous solutions. The ion pairs formed between tri-short chain, mono-long chain quaternary ammonium halides and many anionic surfactants have low solubility and precipitate as a solid salt at typical use concentrations. This not only has a negative effect on cleaning performance, but also prevents use of such anionic-cationic ion pair complexes in isotropic liquid detergents. On the other hand, ion pairs formed by such cationic surfactants and many anionic surfactants in the presence of a bridging surfactant are much more soluble, as detailed herein. This increased solubility allows for greater flexibility in formulating with the bulk surfactant compositions (i.e. the surfactant blends). Surfactant compositions of the instant invention are particularly useful in preparing shampoo and/or body washes which provide superior cleaning, foam generation and/or conditioning properties to the hair or skin. Generally, the inventive surfactant blends are homogeneous phase materials, which are flowable and are transparent to opaque in appearance. The surfactant blends when diluted to a concentration of about 0.1 percent by weight in water generally form a clear aqueous solution substantially free of precipitates at 25° C.

One indication that an anionic-cationic complex is solubilized within the ternary surfactant blends of the invention is the unique surface tension properties exhibited by the ternary surfactant blends. The interfacial surface tension and detergency behavior of an anionic-cationic complex is very different compared to either of the individual anionic and cationic surfactant components. In particular, an anionic-cationic complex exhibits significantly lower interfacial surface tension and significantly higher foaming than either an anionic or cationic surfactant alone. In similar fashion, the interfacial tension between certain oils and an aqueous solution of a ternary surfactant blend of the invention was found to be lower than the interfacial tension between the same oils and an aqueous solution of the individual anionic, cationic, or bridging surfactants, or combinations of two of these surfactants. This indicates that an anionic-cationic complex, once formed, remains solubilized in aqueous solutions of ternary surfactant blends of the invention. Surprisingly, anionic-cationic complexes remain solubilized within aqueous solutions of ternary surfactant blends even when one or both of the cationic and anionic surfactants contain substantially no alkylene oxide groups or additional charges that remain unneutralized during complexation.

Long-term storage stability is often lacking in mixtures employing anionic-cationic complex mixtures due to the tendency of anionic and cationic surfactants in combination to produce precipitates in water. Typically, such compositions are not stable and separate into two phases on storage, rendering them aesthetically and functionally unacceptable. Surprisingly, ternary surfactant blends of this invention are generally provided in the form of a flowable composition that can be expected to be stored for long periods of time prior to sale or use. The formation of an anionic-cationic precipitate is avoided herein, and a lack of such a precipitate in the compositions of this invention is one of this invention's advantages.

More specifically in one embodiment, the present invention provides for a surfactant composition comprising:

(a) from about 0.05% to about 5% by weight based on the total weight of the composition of a cationic surfactant which is a quaternary ammonium compound of the formula:

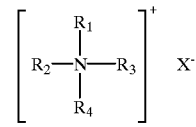

where $R^1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and (b) an anionic surfactant comprising i) from about 3% to about 22% by weight based on the total weight of the composition of an alpha sulfonated alkyl ester of the formula

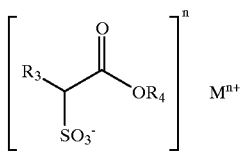

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 11% by weight based on the total weight of the composition of a sulfonated fatty acid of the formula

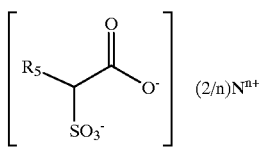

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;

wherein the total concentration of combined cationic, anionic, and bridging surfactants is from about 3% to about 40% by weight based on the total weight of the composition. Preferably, the total concentration of combined cationic, anionic, and bridging surfactants is from about 4% to about 28% by weight based on the total weight of the composition. Further in accordance with this embodiment, the alpha sulfonated alkyl ester somewhat more preferably is of the formula

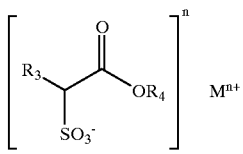

wherein about 25% by weight based on the total weight of the alpha sulfonated alkyl ester of $R_3$ is a $C_{11}$–$C_{14}$ alkyl group and about 75% by weight based on the total weight of the alpha sulfonated alkyl ester of $R_3$ is a mixture of $C_6$–$C_{10}$ and $C_{15}$–$C_{22}$ alkyl groups. Additionally in accordance with this embodiment, the cationic surfactant is preferably cetyl trimethyl ammonium chloride. The surfactant composition may further comprise from about 0.01% to about 15% by weight based on the total weight of the composition of a nonionic surfactant. Preferably, the nonionic surfactant is selected from the group consisting essentially of polyethylene glycol esters, alkanolamides, alkoxylated alcohols or a mixture thereof. These and other optional nonionic surfactants are discussed in more detail below. The surfactant composition may further comprise from about 0.01% to about 20% by weight based on the total weight of the composition of an auxiliary anionic surfactant. Preferably, the auxiliary anionic surfactant is selected from the group consisting essentially of alpha olefin sulfonates, alkyl sulfates, alkyl alkoxy sulfates or a mixture thereof. These and other optional auxiliary anionic surfactants are discussed in more detail below. Additionally, the surfactant composition may further comprise from about 0.01% to about 5% by weight based on the total weight of the composition of an inorganic salt. Preferably, the inorganic salt is selected from the group consisting essentially of sodium chloride, ammonium chloride, magnesium chloride or a mixture thereof. Further in accordance with this embodiment, the composition when diluted to a concentration of about 0.1 percent by weight in water generally forms a clear aqueous solution substantially free of precipitates at 25° C. The viscosity of the composition is generally from about 100 cps to about 30,000 cps, at 25° C.

In another embodiment, the present invention provides a surfactant composition comprising:

(a) from about 0.05% to about 5% by weight based on the total weight of the composition of a cationic surfactant which is a quaternary ammonium compound of the formula:

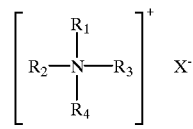

where
$R_1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and (b) an anionic surfactant comprising
i) from about 3% to about 25% by weight based on the total weight of the composition of an alpha sulfonated alkyl ester of the formula

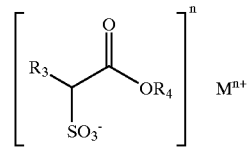

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 15% by weight based on the total weight of the composition of a sulfonated fatty acid of the formula

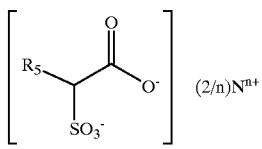

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;

wherein the total concentration of combined cationic, anionic, and bridging surfactants is from about 3% to about 40% by weight based on the total weight of the composition. Somewhat more preferably, the total concentration of combined cationic, anionic, and bridging surfactants is from about 4% to about 30% by weight based on the total weight of the composition. Further in accordance with this embodiment, the alpha sulfonated alkyl ester is of the formula

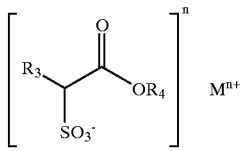

wherein about 25% by weight based on the total weight of the alpha sulfonated alkyl ester of $R_3$ is a $C_{15}$–$C_{22}$ alkyl group and about 75% by weight based on the total weight of the alpha sulfonated alkyl ester of $R_3$ is a $C_6$–$C_{14}$ alkyl group. Additionally in accordance with this embodiment, the cationic surfactant is preferably cetyl trimethyl ammonium chloride. The surfactant composition may further comprise from about 0.01% to about 20% by weight based on the total weight of the composition of a nonionic surfactant. Preferably, the nonionic surfactant is selected from the group consisting essentially of polyethylene glycol esters, alkanolamides, alkoxylated alcohols or a mixture thereof. These and other optional nonionic surfactants are discussed in more detail below. The surfactant composition may further comprise from about 0.01% to about 20% by weight based on the total weight of the composition of an auxiliary anionic surfactant. Preferably the auxiliary anionic surfactant is selected from the group consisting essentially of alpha olefin sulfonates, alkyl sulfates, alkyl alkoxy sulfates or a mixture thereof. These and other optional auxiliary anionic surfactants are discussed in more detail below. Additionally, the surfactant composition may further comprise from about 0.01% to about 5% by weight based on the total weight of the composition of an inorganic salt. Preferably, the inorganic salt is selected from the group consisting essentially of sodium chloride, ammonium chloride, magnesium chloride or a mixture thereof. Further in accordance with this embodiment, the composition when diluted to a concentration of about 0.1 percent by weight in water generally forms a clear aqueous solution substantially free of precipitates at 25° C. The viscosity of the composition is generally from about 100 cps to about 30,000 cps, at 25° C.

In another embodiment, the invention provides methods for preparing ternary surfactant blends. The ternary blends of the invention are readily obtained by merely pre-mixing either the anionic or the cationic surfactant with the bridging surfactant, followed by mixing with the surfactant not pre-mixed. More specifically, in one embodiment the instant invention provides for a method for preparing a ternary surfactant blend comprising combining:

(a) from about 0.05% to about 5% by weight based on the total weight of the composition of a cationic surfactant which is a quaternary ammonium compound of the formula:

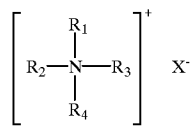

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and (b) an anionic surfactant comprising i) from about 3% to about 22% by weight based on the total weight of the composition of an alpha sulfonated alkyl ester of the formula

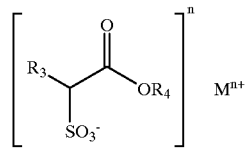

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 11% by weight based on the total weight of the composition of a sulfonated fatty acid of the formula

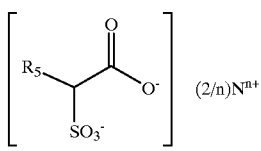

wherein $R_5$ is a C6–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or mixtures thereof; and (d) water;

wherein the total concentration of combined cationic, anionic, and bridging surfactants is from about 3% to about 40% by weight based on the total weight of the composition. Preferably, the total concentration of combined cationic, anionic, and bridging surfactants is from about 4% to about 28% by weight based on the total weight of the composition. Further in accordance with this embodiment, the alpha sulfonated alkyl ester somewhat more preferably is of the formula

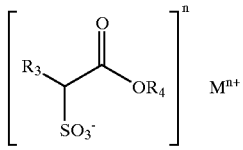

wherein about 25% by weight based on the total weight of the alpha sulfonated alkyl ester of $R_3$ is a $C_{11}$–$C_{14}$ alkyl group and about 75% by weight based on the total weight of the alpha sulfonated alkyl ester of $R_3$ is a mixture of $C_6$–$C_{10}$ and $C_{15}$–$C_{22}$ alkyl groups. Additionally in accordance with this embodiment, the cationic surfactant is preferably cetyl trimethyl ammonium chloride. The method may further comprise combining from about 0.01% to about 15% by weight based on the total weight of the composition of a nonionic surfactant. Preferably, the nonionic surfactant is selected from the group consisting essentially of polyethylene glycol esters, alkanolamides, alkoxylated alcohols or a mixture thereof. These and other optional nonionic surfactants are discussed in more detail below. The method may further comprise combining from about 0.01% to about 20% by weight based on the total weight of the composition of an auxiliary anionic surfactant. Preferably, the auxiliary anionic surfactant is selected from the group consisting essentially of alpha olefin sulfonates, alkyl sulfates, alkyl alkoxy sulfates or a mixture thereof. These and other optional auxiliary anionic surfactants are discussed in more detail below. Additionally, the method may further comprise combining from about 0.01% to about 5% by weight based on the total weight of the composition of an inorganic salt. Preferably, the inorganic salt is selected from the group consisting essentially of sodium chloride, ammonium chloride, magnesium chloride or a mixture thereof. Further in accordance with this embodiment, the composition produced in accordance with this method when diluted to a concentration of about 0.1 percent by weight in water generally forms a clear aqueous solution substantially free of precipitates at 25° C. The viscosity of the composition produced in accordance with this method is generally from about 100 cps to about 30,000 cps, at 25° C.

In another embodiment, the present invention provides for a method for preparing a ternary surfactant blend comprising combining:

(a) from about 0.05% to about 5% by weight based on the total weight of the composition of a cationic surfactant which is a quaternary ammonium compound of the formula:

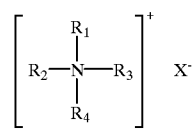

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and (b) an anionic surfactant comprising i) from about 3% to about 25% by weight based on the total weight of the composition of an alpha sulfonated alkyl ester of the formula

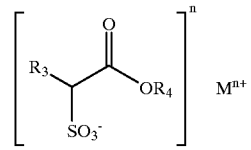

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 15% by weight based on the total weight of the composition of a sulfonated fatty acid of the formula

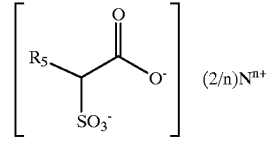

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;

wherein the total concentration of combined cationic, anionic, and bridging surfactants is from about 3% to about 40% by weight based on the total weight of the composition. Somewhat more preferably, the total concentration of combined cationic, anionic, and bridging surfactants is from about 4% to about 30% by weight based on the total weight of the composition. Further in accordance with this embodiment, the alpha sulfonated alkyl ester is of the formula

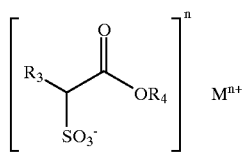

wherein about 25% by weight based on the total weight of the alpha sulfonated alkyl ester of $R_3$ is a $C_{15}$–$C_{22}$ alkyl group and about 75% by weight based on the total weight of the alpha sulfonated alkyl ester of $R_3$ is a $C_6$–$C_{14}$ alkyl group. Additionally in accordance with this embodiment, the cationic surfactant is preferably cetyl trimethyl ammonium chloride. The method may further comprise combining from about 0.01% to about 20% by weight based on the total weight of the composition of a nonionic surfactant. Preferably, the nonionic surfactant is selected from the group consisting essentially of polyethylene glycol esters, alkanolamides, alkoxylated alcohols or a mixture thereof. These and other optional nonionic surfactants are discussed in more detail below. The method may further comprise combining from about 0.01% to about 20% by weight based on the total weight of the composition of an auxiliary anionic surfactant. Preferably the auxiliary anionic surfactant is selected from the group consisting essentially of alpha olefin sulfonates, alkyl sulfates, alkyl alkoxy sulfates or a mixture thereof. These and other optional auxiliary anionic surfactants are discussed in more detail below. Additionally, the method may further comprise combining from about 0.01% to about 5% by weight based on the total weight of the composition of an inorganic salt. Preferably, the inorganic salt is selected from the group consisting essentially of sodium chloride, ammonium chloride, magnesium chloride or a mixture thereof. Further in accordance with this embodiment, the composition produced in accordance with the method when diluted to a concentration of about 0.1 percent by weight in water generally forms a clear aqueous solution substantially free of precipitates at 25° C. The viscosity of the composition produced in accordance with the method is generally from about 100 cps to about 30,000 cps, at 25° C.

In yet another embodiment, the instant invention provides for method of cleaning and/or conditioning hair or skin comprising (a) optionally wetting the skin or hair;

(b) applying to the skin or hair an effective cleaning and/or conditioning amount of a surfactant composition comprising i) from about 0.05% to about 5% by weight based on the total weight of the composition of a cationic surfactant which is a quaternary ammonium compound of the formula:

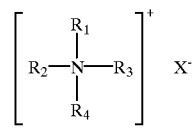

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and ii) an anionic surfactant comprising a) from about 3% to about 22% by weight based on the total weight of the composition of an alpha sulfonated alkyl ester of the formula

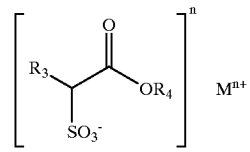

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and b) from about 0.01% to about 11% by weight based on the total weight of the composition of a sulfonated fatty acid of the formula

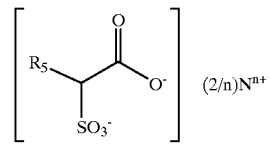

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of a) to b) is from about 10:1 to about 0.5:1; and iii) from about 0.01% to about 15% by weight based on the total weight of the composition a bridging surfactant selected from the group consisting of amine oxides, ethoxamides, and betaines or a mixture thereof; and iv) water;

wherein the total concentration of combined cationic, anionic, and bridging surfactants is from about 3% to about 40% by weight based on the total weight of the composition; and (c) optionally rising the surfactant composition from the skin or hair with water.

Preferably, the total concentration of combined cationic, anionic, and bridging surfactants is from about 4% to about 28% by weight based on the total weight of the composition. Further in accordance with this embodiment, the alpha sulfonated alkyl ester somewhat more preferably is of the formula

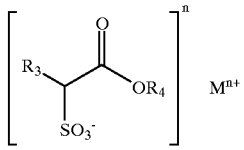

wherein about 25% by weight based on the total weight of the alpha sulfonated alkyl ester of $R_3$ is a $C_{11}$–$C_{14}$ alkyl group and about 75% by weight based on the total weight of the alpha sulfonated alkyl ester of $R_3$ is a mixture of $C_6$–$C_{10}$ and $C_{15}$–$C_{22}$ alkyl groups. Additionally in accordance with this embodiment, the cationic surfactant is preferably cetyl trimethyl ammonium chloride. The surfactant composition may further comprise from about 0.01% to about 15% by weight based on the total weight of the composition of a nonionic surfactant. Preferably, the nonionic surfactant is selected from the group consisting essentially of polyethylene glycol esters, alkanolamides, alkoxylated alcohols or a mixture thereof. These and other optional nonionic surfactants are discussed in more detail below. The surfactant composition may further comprise from about 0.01% to about 20% by weight based on the total weight of the composition of an auxiliary anionic surfactant. Preferably, the auxiliary anionic surfactant is selected from the group consisting essentially of alpha olefin sulfonates, alkyl sulfates, alkyl alkoxy sulfates or a mixture thereof. These and other optional auxiliary anionic surfactants are discussed in more detail below. Additionally, the surfactant composition may further comprise from about 0.01% to about 5% by weight based on the total weight of the composition of an inorganic salt. Preferably, the inorganic salt is selected from the group consisting essentially of sodium chloride, ammonium chloride, magnesium chloride or a mixture thereof.

Additionally, the invention provides a method of cleaning and/or conditioning hair or skin comprising (a) optionally wetting the skin or hair;

(b) applying to the skin or hair an effective cleaning and/or conditioning amount of a surfactant composition comprising i) from about 0.05% to about 5% by weight based on the total weight of the composition of a cationic surfactant which is a quaternary ammonium compound of the formula:

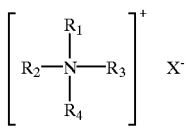

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; and ii) an anionic surfactant comprising a) from about 3% to about 25% by weight based on the total weight of the composition of an alpha sulfonated alkyl ester of the formula

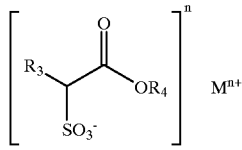

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and b) from about 0.01% to about 15% by weight based on the total weight of the composition of a sulfonated fatty acid of the formula

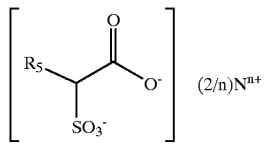

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of a) to b) is from about 10:1 to about 0.5:1; and iii) from about 0.01% to about 15% by weight based on the total weight of the composition a bridging surfactant selected from the group consisting of amine oxides, ethoxamides, and betaines or a mixture thereof; and iv) water; wherein the total concentration of combined cationic, anionic, and bridging surfactants is from about 3% to about 40% by weight based on the total weight of the composition; and (c) optionally rising the surfactant composition from the skin or hair with water.

In accordance with this method, somewhat more preferably, the total concentration of combined cationic, anionic, and bridging surfactants is from about 4% to about 30% by weight based on the total weight of the composition. Further in accordance with this embodiment, the alpha sulfonated alkyl ester is of the formula

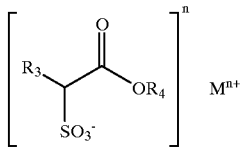

wherein about 25% by weight based on the total weight of the alpha sulfonated alkyl ester of $R_3$ is a $C_{15}$–$C_{22}$ alkyl group and about 75% by weight based on the total weight of the alpha sulfonated alkyl ester of $R_3$ is a $C_6$–$C_{14}$ alkyl group. Additionally in accordance with this embodiment, the cationic surfactant is preferably cetyl trimethyl ammonium chloride. The surfactant composition may further comprise from about 0.01% to about 20% by weight based on the total weight of the composition of a nonionic surfactant. Preferably, the nonionic surfactant is selected from the group consisting essentially of polyethylene glycol esters, alkanolamides, alkoxylated alcohols or a mixture thereof. These and other optional nonionic surfactants are discussed in more detail below. The surfactant composition may further comprise from about 0.01% to about 20% by weight based on the total weight of the composition of an auxiliary anionic surfactant. Preferably the auxiliary anionic surfactant is selected from the group consisting essentially of alpha olefin sulfonates, alkyl sulfates, alkyl alkoxy sulfates or a mixture thereof. These and other optional auxiliary anionic surfactants are discussed in more detail below. Additionally, the surfactant composition may further comprise from about 0.01% to about 5% by weight based on the total weight of the composition of an inorganic salt. Preferably, the inorganic salt is selected from the group consisting essentially of sodium chloride, ammonium chloride, magnesium chloride or a mixture thereof.

In other embodiments, the present invention further encompasses consumer detergent, laundry and personal care products prepared using the surfactant blends detailed herein. The essential, as well as the optional, components of the present invention are described below.

Cationic Surfactants

Generally, the cationic surfactant is a surfactant selected from the group comprising fatty amine salts, fatty diamine salts, polyamine salts, quaternary ammonium salts, polyoxyethyleneated fatty amine salts, quaternized polyoxyethyleneated fatty amines, and mixtures thereof. A variety of cationic surfactants useful in the present invention are well known in the art. Cationic surfactants useful herein include those disclosed in the following documents, all of which are incorporated by reference herein: M. C. Publishing Co., *McCutcheon's Detergents & Emulsifiers*, (North American Ed., 1993); Schwartz et al., *Surface Active Agents, Their Chemistry and Technology*, New York; Interscience Publisher, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983. Suitable anions include but are not limited to halogen, sulfate, methosulfate, ethosulfate, tosylate, acetate, phosphate, nitrate, sulfonate, and carboxylate.

Cationic surfactants in the form of quaternary ammonium salts include mono-long chain alkyl-tri-short chain alkyl ammonium halides, wherein the long chain alkyl group has from about 8 to about 22 carbon atoms and is derived from long-chain fatty acids, and wherein the short chain alkyl groups can be the same or different but preferably are independently methyl or ethyl. Examples of quaternary ammonium salts useful herein include but are not limited to cetyl trimethyl ammonium chloride and lauryl trimethyl ammonium chloride. A particularly preferred quaternary ammonium salt is cetyl trimethyl ammonium chloride.

Salts of primary, secondary and tertiary fatty amines are also suitable cationic surfactant materials. The alkyl groups of such amine salts preferably have from about 12 to about 22 carbon atoms, and may be substituted or unsubstituted. Secondary and tertiary amine salts are preferred, tertiary amine salts are particularly preferred. Suitable amine salts include the halogen (i.e fluoride, chloride, bromide), acetate, phosphate, nitrate, citrate, lactate and alkyl sulfate salts. Amine salts derived from amine, such as for example, stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine, are useful herein. Such salts also include stearylamine hydrogen chloride, soyamine chloride, stearylamine formate, N-tallowpropane diamine dichloride and stearamidopropyl dimethylamine citrate. Additionally cationic surfactants included among those useful in the present invention are disclosed in U.S. Pat. No. 4,275,055, Nachtigal, et al., issued Jun. 23, 1981, incorporated herein by reference.

In addition to the above, cationic surfactants particularly useful herein are those of the general formula:

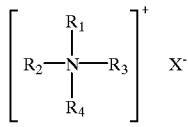

where $R^1$, $R_2$, and $R_3$ are independently ethyl, methyl or benzyl; $R_4$ is an alkyl group having an average of from about 8 to about 18 carbon atoms (preferably 8 to 16 carbon atoms); and X is an a suitable ion including but not limited to halogen, sulfate, methosulfate, ethosulfate, tosylate, acetate, phosphate, nitrate, sulfonate, or carboxylate. Additionally, the alkyl $R_4$ group can be a straight, branched, mid-chain branched or cyclic alkyl group.

Other quaternary ammonium compounds and amine salt compounds include those of the above general formula in the form of ring structures formed by covalently linking two of the radicals. Examples include imidazolines, imidazoliniums, and pyridiniums, etc., wherein said compound has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxooctadecyl)oxy]ethyl]amino]ethyl]pyridinium chloride. Additionally, usefully polymerizable surface active agents include those of the above general formula in the form of ring structures formed by covalently linking two of the $R_1$–$R_4$ groups.

The quaternary ammonium salts of the present invention may be prepared by a variety of methods known to the art, including for example, halide exchange, wherein a halide based quaternary ammonium compound is ion exchanged with X, where X is defined above.

The most preferred cationic surfactants for use in the present invention include octyltrimethyl ammonium chloride, decyltrimethyl ammonium chloride, dodecyltrimethyl ammonium bromide, dodecyltrimethyl ammonium chloride, AMMONYX® CETAC-30, BTC®-65NF, BTC®-835 and BTC®-885, all commercially available from Stepan Company.

Other cationic surfactants includes those compounds commonly referred to as "ester quats", and as disclosed in U.S. Pat. No. 5,939,059 (incorporated herein in its entirety). Typically, such materials are of the general formula

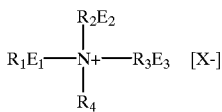

wherein $X^-$ is an anion, $R_1$, $R_2$, $R_3$ can be the same or different and are independently straight or branched chain alkyl groups of from 2 to about 6 carbon atoms; R4 is a saturated or unsaturated, straight or branched chain aliphatic group having from about 1 to about 6 carbon atoms optionally substituted with hydroxy, epoxy or halogen and $E_1$, $E_2$ and $E_3$ can be the same or different at each occurrence and are selected from the group consisting of —H, —OH and aliphatic ester groups of the following formula (II):

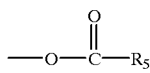

wherein $R_5$ is a saturated or unsaturated, straight or branched chain aliphatic group of from about 11 to about 24 carbon atoms, optionally substituted with hydroxy, epoxy or halogen, provided that at least one of $E_1$, $E_2$ or $E_3$ is a group of formula (II).

Additionally, a quaternary ammonium compound of the formula:

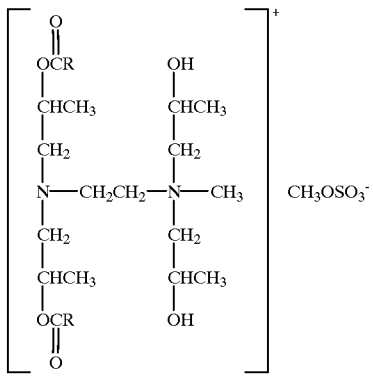

where R is substantially linear nor-oleyl, may be used in the various inventive blends. This material, also called STEPANQUAT® ML, is commercially available from Stepan Company, Northfield, Ill.. Additionally, the cationic surfactant may be a di-quaternary or poly quaternary compound.

Anionic Surfactants

Generally and preferably, the anionic surfactant comprises
a) from about 3% to about 25% by weight based on the total weight of the composition of an alpha sulfonated alkyl ester of the formula

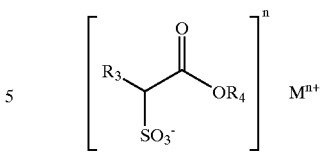

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and
b) from about 0.01% to about 15% by weight based on the total weight of the composition of a sulfonated fatty acid of the formula

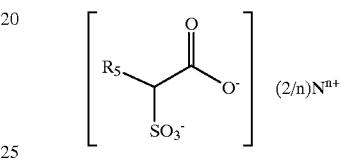

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1. Additionally, the alkyl $R_3$ and/or $R_5$ groups can be a straight, branched, mid-chain branched or cyclic alkyl groups in form.

The alpha sulfonated alkyl esters used in the invention are typically prepared by sulfonating an alkyl ester of a fatty acid with a sulfonating agent such as $SO_3$, followed by neutralization with a base, such as sodium hydroxide, potassium hydroxide, calcium hydroxide, magnesium oxide, monoethanolamine, diethanolamine or triethanolamine, or a mixture thereof. When prepared in this manner, the alpha sulfonated alkyl esters normally contain a minor amount, typically not exceeding 33% by weight, of alpha sulfonated fatty acid, i.e., disalt, which results from hydrolysis of the ester. Generally, larger amounts of the disalt are obtained by hydrolyzing a known amount of the monosalt; hydrolysis may be accomplished in situ during the preparation of the composition. Accordingly, the alpha sulfonated alkyl ester and alpha sulfonated fatty acid may be provided to the composition (or utilized in the inventive process) as a blend of components which naturally result from the sulfonation of an alkyl ester of a fatty acid, or as individual components. Furthermore, it is known to one skilled in the art that minor impurities such as sodium sulfate, unsulfonated methyl esters (ME), and unsulfonated fatty acids (FA) may also be present in the mixtures according to the invention.

The alpha sulfonated alkyl esters, i.e., alkyl ester sulfonate surfactants, include linear esters of $C_6$–$C_{22}$ carboxylic acid (i.e., fatty acids) which are sulfonated with gaseous $SO_3$ according to the "The Journal of American Oil Chemists Society," 52 (1975), pp. 323–329. Suitable starting materials include, among others, natural fatty substances as derived from tallow, palm oil, etc.

Suitable anionic α-sulfonated methyl ester surfactant also include ALPHA STEP® MC-48 or ALPHA STEP® ML-40

(both commercially available from Stepan Company, Northfield, Ill.).

Bridging Surfactants

The bridging surfactants of the present invention are selected from the group consisting of semi-polar nonionic (i.e., amine oxides), ethoxamide, and amphoteric surfactants (i.e., betaines) and mixtures thereof. Especially preferred bridging surfactants include amine oxides, ethoxylated alkanolamides, and betaines.

Semi-polar nonionic surfactants include water-soluble amine oxides having an alkyl moiety containing from about 10 to about 18 carbon atoms and 2 moieties selected from the group consisting of alkyl groups and hydroxyalkyl groups containing from about 1 to about 3 carbon atoms. Semi-polar nonionic surfactants also include water-soluble sulfoxides having alkyl moieties containing from about 10 to about 18 carbon atoms and a moiety selected from the group comprising alkyl groups and hydroxyalkyl groups of from about 1 to about 3 carbon atoms.

The present invention encompasses semi-polar nonionic surfactants that are amine oxides formed as shown in Scheme I, wherein $R_1$, $R_2$, $R_3$ independently are substituted or unsubstituted hydrocarbyl groups of from about 1 to about 30 carbon atoms, or hydrocarbyl groups having from about 1 to about 30 carbon atoms and containing one or more aromatic, ether, ester, amido, or amino moieties present as substituents or as linkages in the radical chain; and wherein $X^-$ is an anion group selected from the group consisting of halogen, sulfonate, sulfate, sulfinate, sulfenate, phosphate, carboxylate, nitrate, and acetate. Additionally, useful semi-polar nonionic surfactants include those of the below general formula in the form of ring structures formed by covalently linking two of the $R_1$–$R_4$ groups. Examples include unsaturated imidazolines, imidazoliniums, and pyridiniums, and the like. Particularly preferred semi-polar nonionic surfactants include alkylamine and amidoamine oxides.

Scheme I: Amine Oxide-Derived Surface Active Agents

Particularly preferred amine oxides include but are not limited to AMMONYX® C8 (octylamine oxide), AMMONYX® C10 (decylamine oxide), AMMONYX® LO (laurylamine oxide), AMMONYX® MO (myristylamine oxide), AMMONYX® MCO (myristyl/cetylamine oxide), and AMMONYX® CDO (cocamidoproylamine oxide), all commercially available from Stepan Company, Northfield, Ill. Amine oxide surfactants which are generally suitable for use in the present invention are alkylamine and amidoamine oxides.

Other Examples of betaines and sultaines which are suitable for use in the present invention are alkyl betaines and sultaines sold as "Mirataine"® by Rhone Poulenc, "Lonzaine"® by Lonza, Inc., Fairlawn, N.J. Examples of betaines and sultaines are cocobetaine, cocoamidoethyl betaine, cocoamidopropyl betaine, lauryl betaine, lauramidopropyl betaine, palmamidopropyl betaine, stearamidopropyl betaine, stearyl betaine, coco-sultaine, lauryl sultaine, tallowamidopropyl hydroxysultaine and the like.

Ethoxamides (also termed ethoxylated alkanolamides or polyethylene glycol amides) suitable for use in the present invention include those having the formula

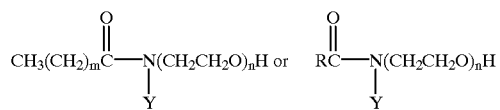

where
RCO— represents the fatty acids derived from coconut oil;
m is an integer from about 8 to about 16;
n has an average value of about 3;
Y is hydrogen or $(CH_2CH_2O)_pH$; and
p is 0, 1 or more.

Preferred ethoxamides include but are not limited to AMIDOX® C-2 (PEG-3 cocamide), AMIDOX® C-5 (PEG-6 cocamide), and AMIDOX® L-5 (PEG-6 lauramide), all commercially available from Stepan Company, Northfield, Ill.

Suitable amphoteric surfactants are selected from the group consisting of alkyl glycinates, propionates, imidazolines, amphoacetates, amphoalkylsulfonates (sold under the tradename Miranol® by Rhone Poulenc), N-alkylaminopropionic acids, N-alkyliminodipropionic acids, imidazoline carboxylates, N-alkybetaines, amido propyl betaines, sarcosinates, cocoamphocarboxyglycinates, amine oxides, sulfobetaines, sultaines and mixtures thereof. Additional suitable amphoteric surfactants include cocoamphoglycinate, cocoamphocarboxyglycinate, lauramphocarboxyglycinate, coco-amphopropionate, lauramphopropionate, stearamphoglycinate, cocoamphocarboxypropionate, tallowamphopropionate, tallowamphoglycinate, oleoamphoglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocamphopropylsulfonate, stearamphopropylsolfonate, oleoampho-propylsulfonate and the like.

Examples of betaines and sultaines which are suitable for use as bridging surfactants are alkyl betaines and sultaines sold under the tradename Mirataine® by Rhone Poulenc, and Lonzaine® by Lonza, Inc., Fairlawn, N.J. Additional examples of betaines and sultaines include cocobetaine, cocoamidoethyl betaine, cocoamidopropyl betaine, lauryl betaine, lauramidopropyl betaine, palmamidopropyl betaine, stearamidopropyl betaine, stearyl betaine, cocosultaine, lauryl sultaine, tallowamidopropyl hydroxysultaine and the like. Particularly preferred amphoteric surfactants include AMPHOSOL® CA (cocamidopropyl betaine) and AMPHOSOL® DM (lauryl betaine), both commercially available from Stepan Company, Northfield, Ill.

Other betaines useful in the present invention include compounds having the formula $R(R_1)_2N^+R_2COO^-$ wherein R is a $C_6$–$C_{18}$ hydrocarbyl group, preferably $C_{10}$–$C_{16}$ alkyl group, each $R_1$ typically $C_1$–$C_3$, alkyl, preferably methyl, and $R_2$ is a $C_1$–$C_5$ hydrocarbyl group, preferably a $C_1$–$C_5$ alkylene group, more preferably a $C_1$–$C_2$ alkylene group. Examples of suitable betaines include coconut acylamidopropyldimethyl betaine; hexadecyl dimethyl betaine; $C_{12}$–$C_{14}$ acylamidopropylbetaine; $C_8$–$C_{14}$ acylamidohexyldiethyl betaine; 4-[$C_{14}$–$C_{16}$ acylmethylamidodiethylammonio]-1-carboxybutane; $C_{16}$–$C_{18}$ acylamidododimethylbetaine; $C_{12}$–$C_{16}$ acylamidopentanediethylbetaine; $C_{12}$–$C_{16}$ acylmethylamidodimethylbetaine. Preferred betaines are $C_{12}$–$C_{18}$ dimethylamoniohexanoate and the $C_{10}$–$C_{18}$ acylamidopropane (or ethane) dimethyl (or diethyl) betaines.

Other sultaines useful in the present invention include compounds having the formula $R(R_1)_2N^+R_2SO_3^-$, wherein R is a $C_6$–$C_{18}$ hydrocarbyl group, preferably a $C_{10}$–$C_{16}$ alkyl group, more preferably a $C_{12}$–$C_{13}$ alkyl group; each $R_1$ is typically $C_1$–$C_3$ alkyl, preferably methyl and $R_2$ is a $C_1$–$C_6$ hydrocabyl group, preferably a $C_1$–$C_3$ alkylene or, preferably, hydroxyalkylene group. Examples of suitable sultaines are $C_{12}$–$C_{14}$ dihydroxyethylammino propane sulfonate, and $C_{16}$–$C_{18}$ dimethylammonio hexane sulfonate, with $C_{12}$–$C_{14}$ amido propyl ammonio-2-hydroxypropyl sultaine being preferred.

Auxiliary Nonionic Surfactants

Although it is preferable that the inventive compositions (and methods to produce such compositions) are free of nonionic surfactants, the inventive compositions may optionally contain auxiliary nonionic surfactants. The auxiliary nonionic surfactants that may be utilized according to the present invention are well known to the art and are described below in a representative manner.

Suitable auxiliary nonionic surfactants in accordance with the present invention are generally disclosed at column, 13 line 14 through column 16, line 6 of U.S. Pat. No. 3,929,678, the disclosure of which is incorporated herein by reference in its entirety. Generally, the auxiliary nonionic surfactant is selected from the group comprising polyoxyethyleneated alkylphenols, polyoxyethyleneated straight chain alcohols, polyoxyethyleneated branched chain alcohols, polyoxyethyleneated polyoxypropylene glycols, polyoxyethyleneated mercaptans, fatty acid esters, glyceryl fatty acid esters, polyglyceryl fatty acid esters, propylene glycol esters, sorbitol esters, polyoxyethyleneated sorbitol esters, polyoxyethylene glycol esters, polyoxyethyleneated fatty acid esters, primary alkanolamides, ethoxylated primary alkanolamides, secondary alkanolamides, ethoxylated secondary alkanolamides, tertiary acetylenic glycols, polyoxyethyleneated silicones, N-alkylpyrrolidones, alkylpolyglycosides, alkylpolylsaccharides, EO-PO blockpolymers, polyhydroxy fatty acid amides, amine oxides and mixtures thereof. Further, exemplary, non-limiting classes of useful auxiliary nonionic surfactants are listed below:

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to 12 carbon atoms in either a straight or branched chain configuration with the alkylene oxide. In a preferred embodiment, the ethylene oxide is present in an amount equal to from about 1 to about 25 moles of ethylene oxide per mole of alkyl phenol. Commercially available auxiliary nonionic surfactants of this type include Igepal® CO-630, marketed by the GAF Corporation; and Triton® X-45, X-1 14, X-100 and X-102, all marketed by the Rohm and Haas Company.

2. The condensation products of aliphatic alcohols with from about 1 to about 25 moles of ethylene oxide. The alkyl chain of the aliphatic alcohol can either be straight or branched, primary or secondary, and generally contain from about 8 to about 22 carbon atoms. Particularly preferred auxiliary nonionics are the condensation products of alcohols having an alkyl group containing from about 6 to about 11 carbon atoms with from about 2 to about 10 moles of ethylene oxide per mole of alcohol. Examples of commercially available auxiliary nonionic surfactants of this type include Tergitol® 15-S-9 (the condensation products of $C_{11}$–$C_{15}$ linear alcohol with 9 moles of ethylene oxide), Tergitol® 24-L-6 NMW (the condensation products of $C_{12}$–$C_{14}$ primary alcohol with 6 moles of ethylene oxide with a narrow molecular weight distribution), both marketed by Union Carbide Corporation; Neodol® 91-8 (the condensation product of $C_9$–$C_{11}$ linear alcohol with 8 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 914-6 (the condensation product of $C_9$–$C_{11}$ linear alcohol with 6 moles of ethylene oxide), marketed by Shell Chemical Company, and Kyro® EOB (the condensation product of $C_{13}$–$C_{15}$ linear alcohol with 9 moles of ethylene oxide), marketed by the Procter and Gamble Company.

3. The condensation products of ethylene oxide with a hydrophobic base formed by the condensation of propylene oxide with propylene glycol. The hydrophobic portion of these compounds preferably has a molecular weight of from about 1500 to about 1880 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic® surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic® compounds, marketed by BASF.

5. Alkylpolysaccharides disclosed in U.S. Pat. No. 4,565,647, Lenado, issued Jan. 21, 1986, incorporated herein by reference, having a hydrophobic group containing from about 6 to about 30 carbon atoms, preferably from about 10 to about 16 carbon atoms and a polysaccharide, e.g., a polyglucoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally, the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

6. An ethyl ester ethoxylate and/or alkoxylate such as those described in U.S. Pat. No. 5,220,046, incorporated herein by reference. These material may be prepared according to the procedure set forth in Japanese Kokai patent application No. HEI 5 [1993]-222396. For example, they may be prepared by a one-step condensation reaction between an alkyl ester and an alkylene oxide in the present of a catalytic amount of magnesium together with another ion selected from the group of $Al^{+3}$, $Ga^{+3}$, $In^{+3}$, $Co^{+3}$, $Sc^{+3}$, $La^{+3}$ and $Mn^{+3}$. Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched, containing from about 8 to about 18, preferably from about 12 to about 14 carbon atoms; n is 2 or 3, preferably 2; t is from about 0 to about 10, preferably 0; and x is from about 1.3 to about 10, preferably from about 1.3 to 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glucosyl units can then be attached between their 1-position and the preceding glycosyl units 2-, 3-, 4- and/or 6-position, preferably predominately the 2-position.

7. Other auxiliary nonionic surfactants include alkoxylated mono- and diglycerides of fatty acids. Preferred are ethoxylated and/or propoxylated glycerides of fatty acids having from 6–40 carbon atoms. Suitable alkoxylated mono- and diglycerides of such acids are commercially available from Witco Corporation. Examples of such auxiliary nonionic surfactants include Varonic LI-63 (PEG-30 Glyceryl Cocoate, Witco), Varonic LI-67 (PEG-80 Glyceryl Cocoate, Witco), Varonic LI-67, 75% (PEG-80 Glyceryl Cocoate, Witco), Varonic LI-42 (PEG-20 Glyceryl Tallowate, Witco), Varonic LI-48 (PEG-80 Glyceryl Tallowate, Witco), and Varonic LI-420, 70% (PEG-200 Glyceryl Tallowate, Witco).

8. Additional auxiliary nonionic surfactants are alkoxylated alkyl esters of fatty acids. Preferred auxiliary alkoxylated alkyl esters are ethoxylated and/or propoxylated methyl esters of fatty acids having from 8–40 carbon atoms. Suitable auxiliary alkoxylated methyl esters of such acids are commercially available from Lion Corporation. Examples of such auxiliary nonionic surfactants include $RCO_2(CH_2CH_2O)_nCH_3$ where R is $C_{12}$, and n is about 10.9 (commercially available from Lion Corporation, Japan, as LC-110 M), and $RCO_2(CH_2CH_2O)_nCH_3$ where R is $C_{12}$, and n is about 14.6 (commercially available from Lion Corporation, Japan, as LC-150M-92).

Auxiliary Anionic Surfactants

Although it is preferable that the sole anionic surfactant be an alpha sulfonated alkyl ester and/or sulfonated fatty acid, the inventive compositions may optionally contain auxiliary anionic surfactants. The auxiliary anionic surfactants that may be utilized according to the present invention are well known to the art and are described below in a representative manner. Generally speaking, a variety of auxiliary anionic surfactants useful in the present invention are well known in the art. Auxiliary anionic surfactants useful herein include those disclosed in the following documents, all of which are incorporated by reference herein: M. C. Publishing Co., *McCutcheon's Detergents & Emulsifiers*, (North American Ed., 1993); Schwartz et al., *Surface Active Agents, Their Chemistry and Technology*, New York; Interscience Publisher, 1949; U.S. Pat. No. 4,285,841, Barrat et al, issued Aug. 25, 1981; and U.S. Pat. No. 3,919,678, Laughlin et al, issued Dec. 30, 1975.

The auxiliary anionic surfactants of the present invention generally include salts (including, for example, sodium, potassium, ammonium, and substituted ammonium salts such as mono-, di-, and triethanolamine salts) of the anionic sulfate, sulfonate, carboxylate and sarcosinate surfactants. Other suitable auxiliary anionic surfactants include the isethionates such as the acyl isethionates, N-acyl taurates, fatty acid amides of methyl tauride, alkyl succinates, sulfoacetates, and sulfosuccinates, monoesters of sulfosuccinate (especially saturated and unsaturated $C_{12}$–$C_{18}$ monoesters), diesters of sulfosuccinate (especially saturated and unsaturated $C_6$–$C_{14}$ diesters), and N-acyl sarcosinates. Resin acids and hydrogenated resin acids are also suitable, such as rosin, hydrogenated rosin, and resin acids and hydrogenated resin acids present in or derived from tallow oil.

Auxiliary anionic sulfate surfactants suitable for use in the compositions of the invention include the linear and branched primary and secondary alkyl sulfates, alkyl ethoxysulfates, fatty oleyl glycerol sulfates, alkyl phenol ethoxylate sulfates, alkyl phenol ethylene oxide ether sulfates, the $C_5$–$C_{17}$ acyl-N—($C_1$–$C_4$ alkyl) and —N—($C_1$–$C_2$ hydroxyalkyl) glucamine sulfates, and sulfates of alkylpolysaccharides such as the sulfates of alkylpolyglucoside.

Auxiliary alkyl sulfate surfactants are preferably selected from the group consisting of the $C_8$–$C_{22}$ alkyl sulfates. Most preferably, the alkyl sulfate surfactant is a $C_8$–$C_{16}$ alkyl sulfate. Alkyl ethoxysulfate surfactants are preferably selected from the group consisting of the $C_8$–$C_{22}$ alkyl sulfates that have been ethoxylated with from about 0.5 to about 30 moles of ethylene oxide per molecule. Most preferably, the alkyl ethoxysulfate surfactant is a $C_8$–$C_{16}$ alkyl sulfate which has been ethoxylated with from about 1 to about 30 moles of ethylene oxide.

A particularly preferred auxiliary anionic surfactant comprises mixtures of $C_8$ alkyl sulfate (POLYSTEP® B-29, commercially available from Stepan Company, Northfield, Ill.) and alkyl ethoxysulfate surfactants. Such mixtures have been disclosed in WO 93/18124, incorporated by reference herein.

Auxiliary anionic sulfonate surfactants suitable for use herein include the salts of $C_5$–$C_{20}$ linear alkylbenzene sulfonates, alkyl ester sulfonates, $C_6$–$C_{22}$ primary or secondary alkane sulfonates, $C_6$–$C_{24}$ olefin sulfonates, alkyl glycerol sulfonates, fatty acyl glycerol sulfonates, fatty oleyl glycerol sulfonates, and any mixtures thereof.

Auxiliary anionic sulfonate surfactants are preferably selected from the group consisting of the $C_8$–$C_{22}$ alkyl sulfonates and $C_8$–$C_{22}$ α-olefin sulfonates. Most preferably, the anionic sulfonate surfactant is an $C_8$–$C_{18}$ alkyl sulfonate, such as BIOTERGE® PAS-8S (commercially available from Stepan Company, Northfield, Ill.), or a $C_{12}$–$C_{18}$ α-olefin sulfonate, such as BIOTERGE® AS-40 (commercially available from Stepan Company, Northfield, Ill.).

Suitable auxiliary anionic carboxylate surfactants include the alkyl ethoxy carboxylates, the alkyl polyethoxy polycarboxylate surfactants and the soaps ("alkyl carboxyls"), especially certain secondary soaps as described herein.

Suitable auxiliary alkyl ethoxy carboxylates include those with the formula $RO(CH_2CH_2O)_xCH_2COO^-M^+$ wherein R is a $C_6$ to $C_{18}$ alkyl group, x ranges from 0 to 10, and the ethoxylate distribution is such that, on a weight basis, the amount of material where x is 0 is less than about 20 percent and M is a cation. Suitable alkyl polyethoxy polycarboxylate surfactants include those having the formula $RO(CHR_1CHR_2O)R_3$ wherein R is a $C_6$ to $C_{16}$ alkyl group, x ranges from 1 to 25, $R_1$ and $R_2$ are selected from the group consisting of hydrogen, methyl acid radical, succinic acid radical, hydroxysuccinic acid radical, and mixtures thereof, and $R_3$ is selected from the group consisting of hydrogen, substituted or unsubstituted hydrocarbon having between 1 and 8 carbon atoms, and mixtures thereof.

Suitable auxiliary anionic soap surfactants include the secondary soap surfactants which contain a carboxyl unit connected to a secondary carbon. Preferred secondary soap surfactants for use herein are water-soluble members selected from the group consisting of the water-soluble salts of 2-methyl-1undecanoic acid, 2-ethyl-1-decanoic acid, 2-propyl-1-nonanoic acid, 2-butyl-1-octanoic acid and 2-pentyl-1-heptanoic acid.

Suitable auxiliary anionic sulfosuccinates include those having the formula

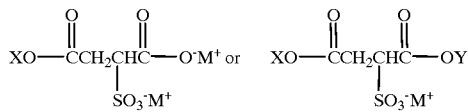

where
X and Y are the same or different and are selected from the group consisting of
R and $R(CH_2CH_2O)_x$, where x has an average value from about 1 to about 30;
R is $C_8$–$C_{22}$ alkyl;
and M is an counterion.

Auxiliary anionic sulfosuccinate surfactants are preferably selected from the group consisting of the $C_8$–$C_{22}$ sulfosuccinates. Most preferably, the auxiliary anionic sulfosuccinate surfactants is a mono-$C_{10}$–$C_{16}$ alkyl sulfosuccinate such as disodium laureth sulfosuccinate (STEPAN-MILD® SL3, commercially available from Stepan Company, Northfield, Ill.)

Other suitable auxiliary anionic surfactants are the sarcosinates of the formula $RCON(R_1)CH_2COOM$, wherein R is a $C_5$–$C_{22}$ linear or branched alkyl or alkenyl group, $R_1$ is a $C_1$–$C_4$ alkyl group and M is an ion. Preferred auxiliary sarcosinate surfactants include but are not limited to the myristyl and oleoyl methyl sarcosinates in the form of their sodium salts. Most preferably, the sarcosinate surfactant is a $C_{10}$–$C_{16}$ sarcosinate such as MAPROSYL® 30 (commercially available from Stepan Company, Northfield, Ill.).

Other suitable auxiliary anionic surfactants are the alkyl sulfoacetates of the formula $RO(CO)CH_2SO_3M$, wherein R is a $C_{12}$–$C_{20}$ alkyl group and M is an ion. Preferred auxiliary alkyl sulfoacetates include but are not limited to the lauryl and myristyl sulfoacetates in the form of their sodium salts. Most preferably, the auxiliary alkyl sulfoacetate is LATHA-NOL® LAL (commercially available from Stepan Company, Northfield, Ill.).

Other Optional Ingredients

The following optional ingredients can be present in various quantities. The ternary surfactant blends may be formulated with optional components, such as fragrances, emollient, solvents, humectants, optical brighteners, thickeners, powders, viscosity modifiers, hydrotropes, preservatives, bluing agents, and dyes, to produce a wide variety of end use products.

Although the use of such optional components is not essential to the present invention, and may in fact be somewhat less preferred depending on the desired final formulation and end use application, suitable optional emollients useful in formulating with blends of the present invention include, for example, stearyl alcohol, glyceryl ricinoleate, glyceryl stearate, propane-1,2-diol, butane-1,3-diol, mink oil, cetyl alcohol, stearamidopropyl dimethylamine, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, dimethicone copolyols, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, and myristyl myristate, and mixtures thereof.

Although generally less preferred, optional solvents useful in formulating with blends of the present invention include, for example, ethyl alcohol, propylene glycol, water, isopropanol, castor oil, ethylene glycol monoethyl ether, diethylene glycol monobutyl ether, diethylene glycol monoethyl ether, dimethyl sulphoxide, dimethyl formamide, and tetrahydrofuran, and mixtures thereof.

Optional humectants useful in formulating with blends of the present invention include, for example, glycerin, sorbitol, sodium 2-pyrrolidone-5-carboxylate, soluble collagen, dibutyl phthalate, propylene glycol, and gelatin, and mixtures thereof.

Optional swellable polymer thickening agents include, for example, methyl cellulose, ethyl cellulose, xanthan gum, gum arabic, gum karaya, guar gum, locust bean gum, ghatti gum, hydrolyzed starches, low molecular weight ethylene oxide polymers, low molecular weight propylene oxide polymers and mixtures thereof.

Optional non-volatile, nonionic silicone conditioning agents suitable for the present invention are selected from the group comprising polyalkyl siloxanes, polyaryl siloxanes, polyalkylaryl siloxanes, polyether siloxane copolymers and mixtures thereof. However, it should also be noted that any silicone fluid having hair conditioning properties may used as an optional ingredient in the present Compositions. The nonvolatile polyalkyl siloxane fluids that may be used include, for example, polydimethylsiloxanes, available, for example, from General Electric Company as SF 1075 methyl phenyl fluid or from Dow Corning as 556 Cosmetic Grade Fluid. The polyether siloxane copolymers that may be used include, for example, a polypropylene oxide modified dimethylpolysiloxane (E.g., Dow Corning DC-1248) although ethylene oxide or mixtures of ethylene oxide and propylene oxide may also be used.

Optional silicone fluids hereof also include polyalkyl or polyaryl siloxanes with the following general formula:

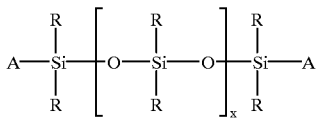

wherein R is alkyl or aryl, and x is an integer form about 7 to about 8,000. "A" represents groups which block the ends of the silicone chains.

The alkyl or aryl groups substituted on the siloxane chain or at the ends of the siloxane chains (A) may have any structure as long as the resulting silicones remain fluid at room temperature, are hydrophobic, are neither irritating, toxic nor otherwise harmful when applied to the hair, are compatible with the other components of the present compositions, are chemically stable under normal use and storage conditions, and are capable of being optionally deposited on and of optionally conditioning the hair.

Suitable A groups include methyl, methoxy, ethoxy, propoxy, and aryloxy. The two R groups on the silicone atom may represent the same or different groups. Preferably, the two R groups represent the same group. Suitable R groups include, for example, methyl, ethyl, propyl, phenyl, methylphenyl and phenylmethyl. The preferred silicones are polydiemethyl siloxane, polydiethyl siloxane and polymethylphenyl siloxane. Polydiemethyl siloxane is especially preferred.

The optional pearlescent/suspending agents suitable for use in the present invention include any of several long chain acyl derivative materials or mixtures of such materials, such as long chain acyl derivatives, long chain amine oxides, and mixtures thereof, wherein such suspending/pearlescent agents are present in the composition in crystalline form. These pearlescent/suspending agents are described in U.S. Pat. No. 4,741,855, Grote and Russell, issued May 3, 1988, the disclosure of which is incorporated herein by reference in its entirety. Included are ethylene glycol esters of fatty acids having from about 16 to about 22 carbon atoms. Preferred are the ethylene glycol stearates, both mono- and distearate, but particularly the distearate containing less than about 7% of the monostearate. Other suspending agents found useful are alkanolamides, preferably with about 16 to about 18 carbon atoms. Preferred alkanolamides are stearic monoethanolamide, stearic diethanolamine, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain ester of long chain alkanol amides (e.g., stearamide DEA distearate, stearamide MEA stearate).

Additional optional pearlescent/suspending agents suitable for use in the present invention are alkyl ($C_{18}$–$C_{22}$) dimethyl amine oxides, such as stearyl dimethyl amine oxide. If the compositions contain an amine oxide or a long chain acyl derivative as a surfactant the pearlescent/suspending function could also be provided by such surfactant and additional pearlescent/suspending agents may not be needed.

Further optional pearlescent/suspending agents that can be used are long chain acyl derivatives, including, for example, N,N-dihydroxycarbyl amido benzoic acid and soluble thereof (e.g., Na and K salts), particularly N,N-di (hydrogenated) $C_{16}$, $C_{18}$ and tallow amido benzoic acid species of this family, which are commercially available from Stepan Company (Northfield, Ill., USA).

Another type of pearlescent/suspending agent which can be used in the present invention is xanthan gum. Xanthan gum is well known to those skilled in the art. For example, hair care compositions utilizing xanthan gum as a pearlescent/suspending agent for the silicone hair conditioning component are described in U.S. Pat. No. 4,788,066, Bolich and Williams, issued Nov. 29, 1988, the disclosure of which is incorporated herein by reference in its entirety. See also, Whistler, Roy L. Editor Industrial Gums—Polysaccharides and Their Derivatives, New York: Academic Press, 1973. Xanthan gum is commercially available from Kelco, a division of Merck & Co., Inc. as Keltrol.

Combinations of long chain acyl derivatives and xanthan gum are disclosed as pearlescent/suspending agents for silicone hair conditioners in U.S. Pat. No. 4,704,272, Oh et al., issued Nov. 3, 1987, both of which are incorporated herein by referenced in their entirety, and may also be used in the present compositions. Gel formulations have high levels of pearlescent/suspending agents relative to pourable, liquid formulations which used as the primary means of imparting gel-like viscosity. Optional gelling agents suitable for use in the present invention include, for example, hydroxy ethylcellulose.

Other optional conditioning agents include sucrogylericide materials, particularly those disclosed in U.S. Pat. No. 5,705,147, issued Jan. 6, 1998 to Stepan Company, incorporated herein in its entirety.

Optional powders useful in formulating with blends of the present invention include, for example, chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, cellulosics such as hydroxyethyl cellulose and sodium carboxymethyl cellulose, ethylene glycol monostearate, zinc or magnesium stearate, zinc oxide and magnesium oxide, and mixtures thereof. These components may also be used as thickeners in fluid or semi-fluid compositions.

Examples of other optional ingredients useful in formulating with blends of the present invention include, for example, volatile and non-volatile silicones; silicone polymers; preservatives, such as para-hydroxy benzoate esters; humectants, such as butane-1,3-diol, glycerol, sorbitol, polyethylene glycol; stabilizers, such as sodium chloride or ammonium chloride; buffer systems, such as lactic acid together with a base such as sodium hydroxide; oils and waxes, such as avocado oil, Evening Primrose oil, mineral oil, petrolatum, sunflower oil, beeswax, ozokerite wax, paraffin wax, lanolin, lanolin alcohol; emollients; thickeners; activity enhancers; colorants; whiteners; fragrances; and bactericides, and mixtures thereof.

The blends of the present invention may also be formulated with optional detergent builder materials. Nearly any detergent builders known in the art can be formulated with the present blends. Examples of useful detergent builders are described in U.S. Pat. Nos. 4,321,165, (to Smith et al, issued Mar. 23, 1982) and 5,565,145 (to Watson et al., issued Oct. 15, 1996), both incorporated herein by reference. Detergent builders can optionally be included in the compositions herein to assist in controlling mineral hardness. Inorganic as well as organic builders can be used. Builders are typically used in fabric laundering compositions to assist in the removal of particulate soils. The level of builder can vary widely depending upon the end use of the composition and its desired physical form. When present in a final formulation, the compositions will typically comprise at least about 1% builder. Liquid formulations typically comprise from about 5% to about 50%, more typically about 5% to about 30%, by weight, of detergent builder. Granular finished formulations typically comprise from about 10% to about 80%, more typically from about 15% to about 50% by weight, of the detergent builder. Lower or higher levels of builder, however, also can be acceptable.

Enzymes and enzyme stabilizers can be formulated with blends of the instant invention for a wide variety of fabric laundering purposes, including removal of protein-based, carbohydrate-based, or triglyceride-based stains, for example, and for fabric restoration. Examples of useful enzymes and enzyme stabilizers are described in U.S. Pat. No. 5,565,145 (to Watson et al., issued Oct. 15, 1996), incorporated herein by reference. Useful enzymes include, for example, proteases, amylases, lipases, and cellulases, as well as mixtures thereof. Other types of enzymes may also be included. They may be of any suitable origin, such as vegetable, animal, bacterial, fungal and yeast origin. However, a particular enzyme choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Suitable examples of proteases are the subtilisins which are obtained from particular strains of B. subtilis and B. licheniforms. Another suitable protease is obtained from a strain of Bacillus, having maximum activity throughout the pH range of 8–12, developed and sold by Novo Industries A/S under the registered trade name ESPERASE. The preparation of this enzyme and analogous enzymes is described in British Pat. Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands). Other proteases include Protease A (see European Patent Application 130,756, published Jan. 9, 1985) and Protease B (see European Patent Application Ser. No. 87303761.8, filed Apr. 28, 1987, and European Patent Application 130,756, Bott et al, published Jan. 9, 1985).

Amylases include, for example, amylases described in British Patent Specification No. 1,296,839 (Novo), RAPIDASE, International Bio-Synthetics, Inc. and TERMAMYL, Novo Industries.

Cellulases suitable for use with ternary surfactant blends of the present invention include both bacterial or fungal cellulase. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from Humicola insolens and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS.247.832CAREZYME (Novo) is especially useful.

Suitable lipase enzymes include those produced by microorganisms of the Pseudomonas group, such as Pseudomonas stutzeri ATCC 19.154, as disclosed in British Patent. 1,372, 034. See also lipases in Japanese Patent Application 53,20487, laid open to public inspection on Feb. 24, 1978. This lipase is available from Amano Pharmaceutical Co. Ltd., Nagoya, Japan, under the trade name Lipase P Amano, hereinafter referred to as Amano-P. Other commercial lipases include Amano-CES, lipases ex Chromobacter viscosum, e.g. Chromobacter viscosum var. lipolyticum NRRLB 3673, commercially available from Toyo Jozo Co., Tagata, Japan; and further Chromobacter viscosum lipases from U.S. Biochemical Corp., U.S.A. and Diosynth Co., The Netherlands, and lipases ex Pseudomonas gladioli. The LIPOLASE enzyme derived from Humicola lanuginosa and commercially available from Novo (see also EPO 341,947) is a preferred lipase for use herein.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985, both. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

The optional enzymes useful herein may be stabilized by the presence of water-soluble sources of calcium and/or magnesium ions in the finished compositions which provide such ions to the enzymes. Calcium ions are generally somewhat more effective than magnesium ions and are preferred herein if only one type of cation is being used. Additional stability can be provided by the presence of various other disclosed stabilizers, especially borate species. See Severson, U.S. Pat. No. 4,537,706. Typical detergents, especially liquids, will comprise from about 1 to about 30, preferably from about 2 to about 20, more preferably from about 5 to about 15, and most preferably from about 8 to about 12, millimoles of calcium ion per liter of finished composition. This concentration can vary somewhat, depending on the amount of enzyme present and its response to the calcium or magnesium ions. The level of calcium or magnesium ions should be selected so that there is always some minimum level available for the enzyme, after allowing for complexation with builders, fatty acids, etc., in the final composition. Any water-soluble calcium or magnesium salt can be used as the source of calcium or magnesium ions, including, but not limited to, calcium chloride, calcium sulfate, calcium malate, calcium maleate, calcium hydroxide, calcium formate, and calcium acetate, and the corresponding magnesium salts. A small amount of calcium ion, generally from about 0.05 to about 0.4 millimoles per liter, is often also present in the final composition due to calcium in the enzyme slurry and formula water. In solid detergent compositions the final formulation may include a sufficient quantity of a water-soluble calcium ion source to provide such amounts in the laundry liquor. In the alternative, natural water hardness may suffice.

Generally, the aforementioned levels of calcium and/or magnesium ions are sufficient to provide enzyme stability to a finished formulation. More calcium and/or magnesium ions can be added to the compositions to provide an additional measure of grease removal performance. Accordingly, final formulations prepared from the blends disclosed herein typically will comprise from about 0.05% to about 2% by weight of a water-soluble source of calcium or magnesium ions, or both. The amount of water-soluble ion can vary with the amount and type of enzyme employed in the final composition.

Final compositions based on the blends detailed herein may also optionally contain various additional stabilizers, especially borate-type stabilizers. Boric acid is preferred, although other compounds such as boric oxide, borax and other borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

Bleaching agents, bleach activators, chelating agents, anti-redeposition agents, polymeric dispersing agents, optical brighteners, suds suppressors, dye transfer inhibition agents, optical brighteners, and soil release agents can be formulated with blends of the instant invention. Examples of such materials are generally described in U.S. Pat. No. 5,565,145 (to Watson et al., issued Oct. 15, 1996), incorporated herein by reference.

Various other detergent additives or adjuvants may be present in the detergent product to give it additional desired properties, either of functional or aesthetic nature. Thus, there may be included in the formulation minor amounts of soil suspending or anti-redeposition agents, e.g. polyvinyl alcohol, fatty amides, sodium carboxymethyl cellulose, hydroxy-propyl methyl cellulose; optical brighteners, e.g. cotton, amine and polyester brighteners, for example, stilbene, triazole and benzidine sulfone compositions, especially, sulfonated substituted triazinyl stilbene, sulfonated naphthotriazole stilbene, benzidine sulfone, etc., most preferred are stilbene and triazole combinations.

Bluing agents such as ultramarine blue; enzymes, preferably proteolytic enzymes, such as subtilisin, bromelin, papain, trypsin and pepsin, as well as amylase type enzymes; bactericides, e.g. tetrachlorosalicylanilide, hexachlorophene; fungicides; dyes; pigments (water dispersible); preservatives; ultraviolet absorbers; anti-yellowing agents, such as sodium carboxymethyl cellulose, complex of $C_{12}$ to $C_{22}$ alkyl alcohol with $C_{12}$ to $C_{18}$ alkylsulfate; pH modifiers and pH buffers; color safe bleaches, perfume, and anti-foam agents or suds suppressors, e.g. silicon compounds, can also be used.

In the case of final formulations, other optional ingredients include neutralizing agents, buffering agents, phase regulants, hydrotropes, polyacids, suds regulants, opacifiers, antioxidants, preservatives, bactericides, dyes, perfumes, and brighteners described in the U.S. Pat. No. 4,285,841, Barrat et al, issued Aug. 25, 1981, incorporated herein by reference. Other ingredients useful in final detergent compositions can be formulated with blends of the instant invention, including carders, processing aids, pigments, solvents for liquid formulations, solid fillers for bar compositions, sodium sulfate, sodium chloride, protein hydrolysates, cholesterol derivatives, UV absorbers, chelating agents, etc. If high sudsing is desired, suds boosters such as the $C_{10}$–$C_{16}$ alkanolamides can be incorporated into the final compositions, typically at 1%–10% levels. The $C_{10}$–$C_{14}$ monoethanol and diethanol amides illustrate a typical class of such suds boosters. If desired, soluble magnesium salts such as $MgCl_2$, $MgSO_4$, and the like, can be added at levels of, typically, 0.1%–2%, to provide additional suds and to enhance grease removal performance to a final formulation.

Additionally, the blends may contain non-conventional surfactants, such as fluorosurfactants, gemini surfactants and polymeric cationic and anionic surfactants. Blends of the present invention are prepared from readily available, economical raw materials, and generally their preparation does not require any special handling or equipment. The blends may be prepared in a batch mode or a continuous mode.

Suitable anti-dandruff agents are selected from the group comprising zinc pyrithione, selenium sulfide, sulfur, coal tar, zinc omadine, piroctone olamine and mixtures thereof.

Suitable preservatives are selected from the group comprising benzyl alcohol, methyl paraben, propyl paraben and imidazolidinyl urea.

Suitable thickeners and viscosity modifiers are selected from the group comprising diethanolamides of long chain fatty acids (e.g., PEG-3 lauramide), block polymers of ethylene oxide and propylene oxide such as Pluronic® F88 offered by BASF, Wyandotte, sodium chloride, sodium sulfate, ammonium xylene sulfonate, ethyl alcohol and polyhydridic alcohols such as, for example, propylene glycol and polyvinyl alcohol.

Suitable gelling agents include, for example, hydroxyethyl cellulose.

Suitable pH adjusting agents are selected from the group comprising citric acid, succinic acid, phosphoric acid, sodium hydroxide, sodium carbonate, etc.

Suitable sequestering agents include, for example, disodium ethylenediamine tetraacetate.

The ternary surfactant blends of the present invention typically contain water as the solvent; however, other solvents may optionally be employed, either alone or in combination with water. Low molecular weight primary or secondary alcohols, exemplified by methanol, ethanol, propanol, and isopropanol, are suitable optional solvents. Monohydric alcohols are preferred optional solvents, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from about 5 to about 90 percent, typically from about 10 to about 50 percent by weight of water and/or optional solvent.

While pH is of secondary significance herein, the ternary surfactant blends of the present invention typically are prepared having a pH of between about 2 and about 10, preferably between about 5 and about 8. Techniques for controlling pH at recommended usage levels include the use of buffers, alkalis, acids, etc., and are well known to those skilled in the art. Suitable materials for adjusting the pH of these compositions include triethanolamine, diethanolamine, sodium carbonate, sodium bicarbonate, and the like.

Ternary surfactant blends of this invention may be formulated into commercially useful products. Ternary surfactant blends of the invention are preferably clear and exhibit no precipitate formation upon aging. Additionally, the ternary surfactant blends may be processed into a variety of forms such as, for example, liquids, solutions, solids, powders, flakes, semi-solids, gels, "ringing" gels, G-phase liquids/pastes, hexagonal liquid crystal phases, or thick non-flowable pastes. The ternary surfactant blends may be spray dried, flaked, or extruded. Although not critical to the present invention, the blends may be prepared "neat" or in a conventional solvent such as water, low molecular weight alcohol or hydrocarbon, or a mixture thereof, to produce a solution of the ternary surfactant blend. The present invention encompasses ternary surfactant systems in dry form and as aqueous solutions. Ternary surfactant blends in concentrations up to 100 percent by weight may be isolated by drying a solution of the blend. Conversely, ternary surfactant blend solutions may be prepared by dissolving a solid form of the blend in water, low molecular weight alcohol, low molecular weight glycol, or mixtures thereof.

One skilled in the art will recognize that modifications may be made in the present invention without deviating from the spirit or scope of the invention. The invention is illustrated further by the following examples, which are not to be construed as limiting the invention or scope of the specific procedures or compositions described herein. All documents, e.g., patents and journal articles, cited above or below are hereby incorporated by reference in their entirety.

As used in the Examples appearing below, the following designations, symbols, terms and abbreviations have the indicated meanings:

| Material | Definition |
|---|---|
| ALPHA-STEP ® PC-48 | Sodium alphasulfo methyl $C_{12-18}$ ester (and) disodium alphasulfo $C_{12-18}$ fatty acid salt (commercially available from Stepan Company, Northfield, Illinois) |
| ALPHA-STEP ® MP-60 | Sodium alphasulfo methyl $C_{12-18}$ ester (and) disodium alphasulfo $C_{12-18}$ fatty acid salt (commercially available from Stepan Company, Northfield, Illinois) |
| STEOL ® CS-330 | Sodium laureth sulfate (3EO) (commercially available from Stepan Company, Northfield, Illinois) |
| AMMONYX ® CETAC-30 | Cetyltrimethylammonium chloride (commercially available from Stepan Company, Northfield, Illinois) |
| AMMONYX ® LO | Lauramine oxide (commercially available from Stepan Company, Northfield, Illinois) |
| AMMONYX ® HCDO | Hydrogenated cocoamidopropyl amine oxide (commercially available from Stepan Company, Northfield, Illinois) |
| AMPHOSOL ® CA | Cocamidopropyl betaine (commercially available from Stepan Company, Northfield, Illinois) |
| AMPHOSOL ® HCG | Hydrogenated cocamidopropyl betaine (commercially available from Stepan Company, Northfield, Illinois) |
| NINOL ® LMP | Lauramide MEA (commercially available from Stepan Company, Northfield, Illinois) |
| AMMONYX ® GA | Dipalmitoylethylhydroxyeyhyl-moniummethosulfate (commercially available from Stepan Company, Northfield Illinois) |
| STEPAN™ PEG 6000 DS | Polyethylene glycol disterarate (commercially available from Stepan Company, Northfield, Illinois) |
| STEPANQUAT ™ ML | Quaternary ammonium salt prepared by reacting oleic acid with Quadrol (NNNN-tetrakis(2-hydroxypropyl) ethylene-diamine), followed by quaternization with dimethylsulfate (commercially available from Stepan Company, Northfield, Illinois) |

One skilled in the art will recognize that modifications may be made in the present invention without deviating from the spirit or scope of the invention. The invention is illustrated further by the following examples, which are not to be construed as limiting the invention or scope of the specific procedures or compositions described herein. In the following examples, all amounts are stated in percent by weight of active material unless indicated otherwise.

EXAMPLE 1

Several surfactant blends as shown in TABLE 1 were prepared by mixing at 25° C. an anionic surfactant, a cationic surfactant, and a bridging surfactant. Appearance and stability were evaluated for each blend. The surfactant blends form a clear aqueous solution free of precipitate.

TABLE 1

| Formulation 1–2 | | #1 | #2 |
|---|---|---|---|
| Total Concentration: | | 12% | 33.6% |
| ALPHA-STEP ® PC48 | | 7 | 19.6 |
| AMPHOSOL ® CA | | 4 | 11.2 |
| AMMONYX ® CETAC-30 | | 1 | 2.8 |
| DI water | | qs100 | qs100 |
| appearance | | clear | clear |
| stability | 25° C. | 6 weeks | |
| | 43° C. | 6 weeks | |

| Formulation 3–4 | | #3 | #4 |
|---|---|---|---|
| Total Concentration: | | 12% | 34.8% |
| ALPHA-STEP ® PC-48 | | 7.5 | 21.75 |
| AMPHOSOL ® CA | | 3.5 | 10.15 |
| AMMONYX ® CETAC-30 | | 1 | 2.9 |
| DI water | | qs100 | qs100 |
| Appearance | | clear | clear |
| stability | 25° C. | 6 weeks | |
| | 43° C. | 6 weeks | |

| Formulation 5–6 | | #5 | #6 |
|---|---|---|---|
| Total Concentration: | | 12% | 33.6% |
| ALPHA-STEP ® PC-48 | | 7.5 | 21 |
| AMPHOSOL ® HCG | | 3.5 | 9.8 |
| AMMONYX ® CETAC-30 | | 1 | 2.8 |
| appearance | | clear | clear |
| stability | 25° C. | 6 weeks | |
| | 43° C. | 6 weeks | |

| Formulation 7–8 | | #7 | #8 |
|---|---|---|---|
| Total Concentration: | | 12% | 33.6% |
| ALPHA-STEP ® PC-48 | | 7 | 19.6 |
| AMMONYX ® LO | | 4 | 11.2 |
| AMMONYX ® CETAC-30 | | 1 | 2.8 |
| appearance | | clear | clear |
| stability, | 25° C. | 6 weeks | |
| | 43° C. | 6 weeks | |

| Formulation 9–10 | | #9 | #10 |
|---|---|---|---|
| Total Concentration: | | 12% | 33.6% |
| ALPHA-STEP ® PC-48 | | 3 | 8.4 |
| STEOL ® CS-330 | | 5 | 14 |
| AMMONYX ® HCDO | | 3 | 8.4 |
| AMMONYX ® CETAC-30 | | 1 | 2.8 |
| appearance | | clear | clear |
| stability | 25° C. | 6 weeks | |
| | 43° C. | 6 weeks | |

| Formulation 11–12 | | #11 | #12 |
|---|---|---|---|
| Total Concentration: | | 32% | 25% |
| ALPHA-STEP ® MC-48 | | 18 | 15 |
| AMPHOSOL ® CA | | 9 | 7.5 |
| AMMONYX ® CETAC-30 | | 5 | |
| STEPANQUAT ™ ML | | | 2.5 |
| appearance | | clear | clear |
| stability | 25° C. | 6 weeks | 6 weeks |
| | 43° C. | 6 weeks | 6 weeks |

EXAMPLE 2

Several surfactant blends as shown in TABLE 2 were prepared by mixing at 50° C. an anionic surfactant, a cationic surfactant, and a bridging surfactant. Appearance and stability were evaluated for each blend. The surfactant blends form a clear aqueous solution free of precipitates

TABLE 2

| Formulation 13–14 | | #13 % active | #14 % active |
|---|---|---|---|
| Total Concentration: | | 12% | 31% |
| ALPHA-STEP ® MP-60 | | 8.25 | 21.45 |
| AMMLPHOSOL ® CA | | 3.5 | 9.1 |
| AMMONYX ® CETAC-30 | | 0.25 | 0.65 |
| DI water | | qs100 | qs100 |
| appearance | | clear | clear |
| stability | 25° C. | 6 weeks | |
| | 43° C. | 6 weeks | |
| Formulation 15–16 | | #15 | #16 |
| Total Concentration | | 12% | 31% |
| ALPHA-STEP ® MP-60 | | 8.25 | 21.45 |
| AMPHOSOL ® CA | | 3.5 | 9.1 |
| AMMONYX ® GA | | 0.25 | 0.65 |
| DI water | | qs100 | qs100 |
| appearance | | clear | clear |
| stability 25° C. | 6 weeks | | |
| | 43° C. | 6 weeks | |
| Formulation 17–18 | | #17 | #18 |
| Total Concentration: | | 12% | 36% |
| ALPHA-STEP ® PC48 | | 7 | 21 |
| AMPHOSOL ® CA | | 4 | 12 |
| AMMONYX ® GA | | 1 | 3 |
| DI water | | qs100 | qs100 |
| appearance | | clear | clear |
| stability 25° C. | 6 weeks | | |
| | 43° C. | 6 weeks | |

EXAMPLE 3

The surfactant blends as shown in TABLE 3 were prepared by mixing at 25° C. an anionic surfactant, a cationic surfactant, and a bridging surfactant. The viscosity profile (salt curve) of each blend was measured using the Brookfield Viscosimeter, Model LVF at 25° C. As can be seen, significant improvement of the viscosity is shown for the anionic, bridge based surfactant composition by the incorporation of the cationic surfactant. The cationic surfactant is a critical ingredient for building the viscosity of the formulation. It is possible to also maintain the clarity and the stability of the formulation.

TABLE 3

| | #19 | #20 | #21 |
|---|---|---|---|
| Formulation 19, 20, 21 | % active | % active | % active |
| ALPHA-STEP ® PC48 | 7 | 8 | 7 |
| AMPHOSOL ® CA | 4 | 4 | 5 |
| AMMONYX ® CETAC-30 | 1 | 0 | 0 |
| total active | 12% | 12% | 12% |
| DI water | qs100 | qs100 | qs100 |
| appearance | clear | clear | clear |
| viscosity profile at 25° C. | | | |
| 0.00% NaCl | 400 | 10 | 30 |
| 1.00% NaCl | 4300 | 60 | 70 |
| 2.00% NaCl | 11850 | 40 | 350 |
| 3.00% NaCl | 14100 | 110 | 1550 |
| 4.00% NaCl | 9200 | 390 | 4020 |

EXAMPLE 4

The surfactant blend as shown in TABLE 4 was prepared by mixing at 50° C. an anionic surfactant, a cationic surfactant, and a bridging surfactant. The salon evaluation of this sample demonstrates the development efficacious anionic-cationic shampoo systems.

The procedure for the salon evaluation include the following steps:

1. Comb dry hair and divide into 2 sections (half head)
2. Wet hair
3. Apply 4 mls of each shampoo (control on one side, experimental on other side).
4. Wash each side using eight circular motions to work up foam.
5. Rinse with tap water for ten seconds
6. Shampooing is repeated using 2 mls of shampoo
7. Rinse for ten seconds
8. Shampoo is evaluated for foam volume and type (density/stability, etc.) and rinsability after each shampooing
9. After second shampooing, hair is evaluated for detangling and wet combability properties, using rubber comb.
10. The hair is blown dry and evaluated for dry combability, static, body and shine Scoring:

0—No difference
1—Slightly better but have to search
2—Noticeable difference
3—Obvious difference

TABLE 4

| Formulation 22 | #22 |
|---|---|
| Total Concentration | 12% |
| ALPHA-STEP ® MP-60 | 8.25 |
| AMPHOSOL ® -CA | 3.5 |
| AMMONYX ® GA | 0.25 |
| DI water | qs100 |
| appearance | clear |

Salon Evaluation

Shampoo Formulation 22 from Table 4 above was compared to a leading national brand shampoo, the results of which are shown below in Application Section 1. Ten heads of hair were washed using the half head method described above, using the scoring system described above.

| Application Section 1 | | |
|---|---|---|
| | | Comments |
| Amount Used: | 4 mL | |
| Flash Foam: | 0000000000 | Equal |
| Volume: | -10-10-1-1-2-1-1-1 | Formula 20 has better foam than national brand |
| Stability: | 0000000000 | Equal |
| Density: | 0000000000 | Equal |
| Rinsability: | 0000000000 | Equal |
| Amount Used: | 2 mL | |
| Flash Foam: | 0000000000 | Equal |
| Volume: | -2-1-2-1-2-2-2-1-2-2 | Formula 20 has significantly better foam than national brand |
| Stability: | 0000000000 | Equal |
| Density: | 0000000000 | Equal |
| Rinsability: | 0000000000 | Equal |
| Detangling: | -20-10-2-1-1000 | Formula 20 is better for detangling than national brand |

-continued

Application Section 1

| | | Comments |
|---|---|---|
| Wet Combability: | -1-2-2-2-2-2-1-10-1 | Formula 20 is noticeably better for wet combability over nat. brand |
| Dry Combability: | -1-1-1-2-2-2-1-1-1-1 | Formula 20 is noticeably better for wet combability over nat. brand |
| Absence of Static: | 000-1000000 | Equal |
| Body: | 0000000000 | Equal |
| Shine: | 0000000000 | Equal |

EXAMPLE 5

The surfactant blend as shown in TABLE 5 was prepared by mixing at 50° C. an anionic surfactant, a cationic surfactant, a bridging surfactant, and an additional nonionic surfactant (lauramide MEA). Appearance and stability were evaluated. The surfactant blends form a clear aqueous solution free of precipitates. The viscosity profile (salt curve) of the blend was measured using the Brookfield Viscosimeter, Model LVF at 25° C. Significant improvements in viscosity were achieved for the anionic, bridge based surfactant composition by the incorporation of the cationic surfactant. The salon evaluation of this sample, also demonstrates that the development of efficacious anionic-cationic shampoo systems.

TABLE 5

| Formulation 23 | % active |
|---|---|
| ALPHA-STEP ® PC48 | 6.5 |
| AMPHOSOL ® CA | 4 |
| AMMONYX ® CETAC-30 ® | 0.5 |
| NINOL ® LMP | 0.5 |
| total active | 12% |
| DI water | qs100 |
| appearance | clear |
| viscosity profile at 25° C. | |
| 0.00% NaCl | 400 |
| 1.00% NaCl | 5400 |
| 2.00% NaCl | 9500 |
| 3.00% NaCl | 5000 |
| 4.00% NaCl | 1700 |

Salon Evaluation

Shampoo Formulation 23 from Table 4 above was compared to second and third leading national brand shampoos, the results of which are shown below in Application Section 2 and 3, respectively below. Ten heads of hair were washed using the half head method described above, using the scoring system described above.

Application Section 2

| | | Comments |
|---|---|---|
| Amount Used: | 4 mL | |
| Flash Foam: | 0112011000 | Formula 21 is better than national brand #2. |
| Volume: | 2333222232 | Formulation 21 is significantly better than national brand #2 |

-continued

Application Section 2

| | | Comments |
|---|---|---|
| Stability: | 0000000000 | Equal |
| Density: | 0000000000 | Equal |
| Rinsability: | 2221111111 | Formulation 21 is significantly better than national brand #2 |
| Amount Used: | 2 mL | |
| Flash Foam: | 0112111001 | Formula 21 is better than national brand #2. |
| Volume: | 3333222332 | Formulation 21 is significantly better than national brand #2 |
| Stability: | 0000000000 | Equal |
| Density: | 0000000000 | Equal |
| Rinsability: | 2112111111 | Formula 21 is better than national brand #2. |
| Detangling: | 2111112200 | Formula 21 is better than national brand #2. |
| Wet Compatibility: | 2221222201 | Formula 21 is better than national brand #2. |
| Dry Compatibility: | 1111211211 | Formula 21 is better than national brand #2. |
| Absence of Static: | 0000000000 | Equal |
| Body: | 1000000000 | Equal |
| Shine: | 0000000000 | Equal |

Application Section 3

| | | Comments |
|---|---|---|
| Amount Used: | 4 mL | |
| Flash Foam: | 0000000000 | Equal |
| Volume: | 0000000000 | Equal |
| Stability: | 0000000000 | Equal |
| Density: | 0000000000 | Equal |
| Rinsability: | 0000000000 | Equal |
| Amount Used: | 2 mL | |
| Flash Foam: | 0000000000 | Equal |
| Volume: | 00-2-2-2-20-2-10 | Formula 21 is significantly better national brand #3 |
| Stability: | 0000000000 | Equal |
| Density: | 0000000000 | Equal |
| Rinsability: | 0000000000 | Equal |
| Detangling: | 0100000000 | Equal |
| Wet Compatibility: | 210-2000000 | Equal |
| Dry Compatibility: | 200-2000000 | Equal |
| Absence of Static: | -2000000000 | Equal |
| Body: | 00-100-20000 | Formulation 21 is better than national brand #3 |
| Shine: | 0000000000 | Equal |

EXAMPLE 6

The surfactant blend as shown in TABLE 6 was prepared by mixing at 50° C. an anionic surfactant, a cationic surfactant, a bridging surfactant and additional nonionic surfactants (polyethylene glycol distearate and lauramide MEA). Appearance, stability and the viscosity profile were evaluated . The surfactant blends form a clear aqueous solution free of precipitates with a competitive salt curve.

| Formulation 24 | % active |
|---|---|
| ALPHA-STEP ® PC48 | 7 |
| AMPHOSOL ® -CA | 3.5 |
| AMMONYX ® CETAC-30 | 0.5 |
| NINOL ® LMP | 0.5 |
| PEG 6000 DS | 0.17 |

-continued

| Formulation 24 | % active |
|---|---|
| total active | 11.67 |
| DI water | qs100 |
| appearance | clear |
| viscosity profile at 25° C. | |
| 0.00% NaCl | 350 |
| 1.00% NaCl | 8750 |
| 2.00% NaCl | 15000 |
| 3.00% NaCl | 15800 |
| 4.00% NaCl | 11550 |

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What is claimed is:

1. A surfactant composition comprising:

(a) from about 0.05% to about 5% by weight based on the total weight of the composition of a cationic surfactant which is a quaternary ammonium compound of the formula:

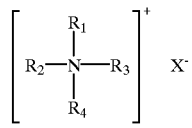

where
$R_1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and (b) an anionic surfactant comprising
   i) from about 3% to about 22% by weight based on the total weight of the composition of an alpha sulfonated alkyl ester of the formula

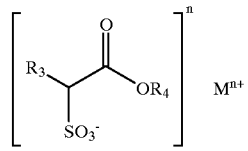

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and ii) from about 0.01% to about 11% by weight based on the total weight of the composition of a sulfonated fatty acid of the formula

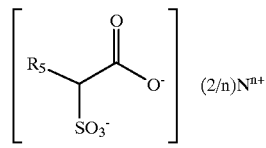

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and
wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;
wherein the total concentration of combined cationic, anionic, and bridging surfactants is from about 3% to about 40% by weight based on the total weight of the composition.

2. A surfactant composition according to claim 1, wherein the alpha sulfonated alkyl ester is of the formula

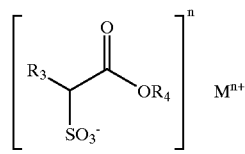

wherein about 25% by weight based on the total weight of the alpha sulfonated alkyl ester of $R_3$ is a $C_{11}$–$C_{14}$ alkyl group and about 75% by weight based on the total weight of the alpha sulfonated alkyl ester of $R_3$ is a mixture of $C_6$–$C_{10}$ and $C_5$–$C_{22}$ alkyl groups.

3. A surfactant composition according to claim 2, wherein the cationic surfactant is cetyl trimethyl ammonium chloride.

4. A surfactant composition according to claim 1, further comprising from about 0.01% to about 15% by weight based on the total weight of the composition of a nonionic surfactant.

5. A surfactant composition according to claim 4, wherein the nonionic surfactant is selected from the group consisting essentially of polyethylene glycol esters, alkanolamides, alkoxylated alcohols or a mixture thereof.

6. A surfactant composition according to claim 4, further comprising from about 0.01% to about 20% by weight based on the total weight of the composition of an auxiliary anionic surfactant.

7. A surfactant composition according to claim 6, wherein the auxiliary anionic surfactant is selected from the group consisting essentially of alpha olefin sulfonates, alkyl sulfates, alkyl alkoxy sulfates or a mixture thereof.

8. A surfactant composition according to claim 6, further comprising from about 0.01% to about 5% by weight based on the total weight of the composition of an inorganic salt.

9. A surfactant composition according to claim 8, wherein the inorganic salt is selected from the group consisting essentially of sodium chloride, ammonium chloride, magnesium chloride or a mixture thereof.

10. A surfactant composition according to claim 1, wherein the composition when diluted to a concentration of about 0.1 percent by weight in water forms a clear aqueous solution substantially free of precipitates at 25° C.

11. A surfactant composition according to claim 1, wherein the viscosity of the composition is from about 100 cps to about 30,000 cps, at 25° C.

12. A surfactant composition according to claim 1, wherein the total concentration of combined cationic, anionic, and bridging surfactants is from about 4% to about 28% by weight based on the total weight of the composition.

13. A surfactant composition comprising:
(a) from about 0.05% to about 5% by weight based on the total weight of the composition of a cationic surfactant which is a quaternary ammonium compound of the formula:

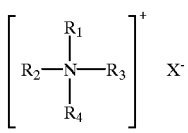

where
$R_1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and (b) an anionic surfactant comprising
i) from about 3% to about 25% by weight based on the total weight of the composition of an alpha sulfonated alkyl ester of the formula

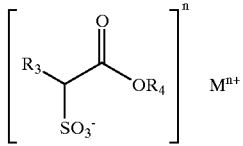

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and
ii) from about 0.01% to about 15% by weight based on the total weight of the composition of a sulfonated fatty acid of the formula

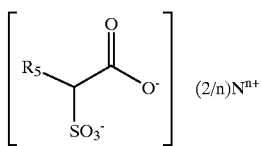

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and
wherein the weight ratio of i) to ii) is from about 10:1 to about 0.5:1; and (c) from about 0.01% to about 15% by weight based on the total weight of the composition a bridging surfactant selected from the group consisting of amine oxides, ethoxamides, and betaines or a mixture thereof; and (d) water;
wherein the total concentration of combined cationic, anionic, and bridging surfactants is from about 3% to about 40% by weight based on the total weight of the composition.

14. A surfactant composition according to claim 13, wherein the alpha sulfonated alkyl ester is of the formula

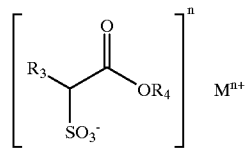

wherein about 25% by weight based on the total weight of the alpha sulfonated alkyl ester of $R_3$ is a $C_{15}$–$C_{22}$ alkyl group and about 75% by weight based on the total weight of the alpha sulfonated alkyl ester of $R_3$ is a $C_6$–$C_{14}$ alkyl group.

15. A surfactant composition according to claim 14, wherein the cationic surfactant is cetyl trimethyl ammonium chloride.

16. A surfactant composition according to claim 13, further comprising from about 0.01% to about 20% by weight based on the total weight of the composition of a nonionic surfactant.

17. A surfactant composition according to claim 16, wherein the nonionic surfactant is selected from the group consisting essentially of polyethylene glycol esters, alkanolamides, alkoxylated alcohols or a mixture thereof.

18. A surfactant composition according to claim 16, further comprising from about 0.01% to about 20% by weight based on the total weight of the composition of an auxiliary anionic surfactant.

19. A surfactant composition according to claim 18, wherein the auxiliary anionic surfactant is selected from the group consisting essentially of alpha olefin sulfonates, alkyl sulfates, alkyl alkoxy sulfates or a mixture thereof.

20. A surfactant composition according to claim 18, further comprising from about 0.01% to about 5% by weight based on the total weight of the composition of an inorganic salt.

21. A surfactant composition according to claim 20, wherein the inorganic salt is selected from the group consisting essentially of sodium chloride, ammonium chloride, magnesium chloride or a mixture thereof.

22. A surfactant composition according to claim 13, wherein the composition when diluted to a concentration of about 0.1 percent by weight in water forms a clear aqueous solution substantially free of precipitates at 25° C.

23. A surfactant composition according to claim 13, wherein the viscosity of the composition is from about 200 cps to about 30,000 cps, at 25° C.

24. A surfactant composition according to claim 13, wherein the total concentration of combined cationic, anionic, and bridging surfactants is from about 4% to about 30% by weight based on the total weight of the composition.

25. A method for preparing a ternary surfactant blend comprising combining:
(a) from about 0.05% to about 5% by weight based on the total weight of the composition of a cationic surfactant which is a quaternary ammonium compound of the formula:

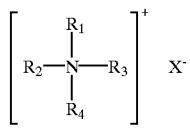

where
R$_1$, R$_2$, and R$_3$ are independently ethyl, methyl or benzyl;
R$_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and
(b) an anionic surfactant comprising
i) from about 3% to about 22% by weight based on the total weight of the composition of an alpha sulfonated alkyl ester of the formula

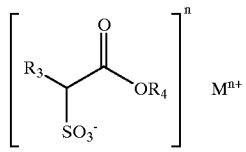

wherein R$_3$ is a C$_6$–C$_{22}$ hydrocarbyl group, an alkyl group, or combination thereof, R$_4$ is a straight or branched chain C$_1$–C$_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and
ii) from about 0.01% to about 11% by weight based on the total weight of the composition of a sulfonated fatty acid of the formula

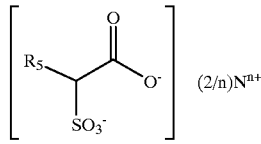

wherein R$_5$ is a C$_6$–C$_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and
wherein the weight ratio of i) to ii) is from about 10:1 to about 0.5:1; and
(c) from about 0.01% to about 15% by weight based on the total weight of the composition a bridging surfactant selected from the group consisting of amine oxides, ethoxamides, and betaines or mixtures thereof; and (d) water;
wherein the total concentration of combined cationic, anionic, and bridging surfactants is from about 3% to about 40% by weight based on the total weight of the composition.

26. A method according to claim 25, wherein the alpha sulfonated alkyl ester is of the formula

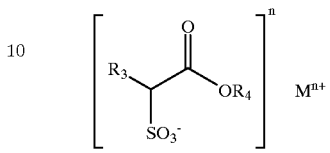

wherein about 25% by weight based on the total weight of the alpha sulfonated alkyl ester of R$_3$ is a C$_{11}$–C$_{14}$ alkyl group and about 75% by weight based on the total weight of the alpha sulfonated alkyl ester of R$_3$ is a mixture of C$_6$–C$_{10}$ and C$_{15}$–C$_{22}$ alkyl groups.

27. A method according to claim 26, wherein the cationic surfactant is cetyl trimethyl ammonium chloride.

28. A method according to claim 25, further comprising combining from about 0.01% to about 15% by weight based on the total weight of the composition of a nonionic surfactant.

29. A method according to claim 28, wherein the nonionic surfactant is selected from the group consisting essentially of polyethylene glycol esters, alkanolamides, alkoxylated alcohols or a mixture thereof.

30. A method according to claim 28, further comprising combining from about 0.01% to about 20% by weight based on the total weight of the composition of an auxiliary anionic surfactant.

31. A method according to claim 30, wherein the auxiliary anionic surfactant is selected from the group consisting essentially of alpha olefin sulfonates, alkyl sulfates, alkyl alkoxy sulfates or a mixture thereof.

32. A method according to claim 30, further comprising combining from about 0.01% to about 5% by weight based on the total weight of the composition of an inorganic salt.

33. A method according to claim 32, wherein the inorganic salt is selected from the group consisting essentially of sodium chloride, ammonium chloride, magnesium chloride or a mixture thereof.

34. A method according to claim 25, wherein the composition when diluted to a concentration of about 0.1 percent by weight in water forms a clear aqueous solution substantially free of precipitates at 25° C.

35. A method according to claim 25, wherein the viscosity of the composition is from about 100 cps to about 30,000 cps, at 25° C.

36. A method according to claim 25, wherein the total concentration of combined cationic, anionic, and bridging surfactants is from about 4% to about 28% by weight based on the total weight of the composition.

37. A method for preparing a ternary surfactant blend comprising combining:
(a) from about 0.05% to about 5% by weight based on the total weight of the composition of a cationic surfactant which is a quaternary ammonium compound of the formula:

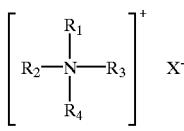

where
R$_1$, R$_2$, and R$_3$ are independently ethyl, methyl or benzyl;
R$_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and
(b) an anionic surfactant comprising
  i) from about 3% to about 25% by weight based on the total weight of the composition of an alpha sulfonated alkyl ester of the formula

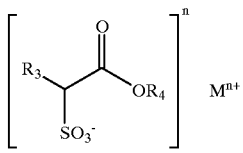

wherein R$_3$ is a C$_6$–C$_{22}$ hydrocarbyl group, an alkyl group, or combination thereof, R$_4$ is a straight or branched chain C$_1$–C$_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and
  ii) from about 0.01% to about 15% by weight based on the total weight of the composition of a sulfonated fatty acid of the formula

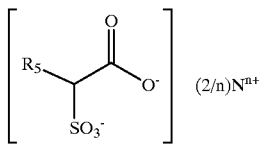

wherein R$_5$ is a C$_6$–C$_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and
  wherein the weight ratio of i) to ii) is from about 10:1 to about 0.5:1; and
(c) from about 0.01% to about 15% by weight based on the total weight of the composition a bridging surfactant selected from the group consisting of amine oxides, ethoxamides, and betaines or a mixture thereof; and
(d) water;
wherein the total concentration of combined cationic, anionic, and bridging surfactants is from about 3% to about 40% by weight based on the total weight of the composition.

38. A method according to claim 37, wherein the alpha sulfonated alkyl ester is of the formula

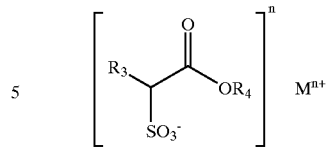

wherein about 25% by weight based on the total weight of the alpha sulfonated alkyl ester of R$_3$ is a C$_{15}$–C$_{22}$ alkyl group and about 75% by weight based on the total weight of the alpha sulfonated alkyl ester of R$_3$ is a C$_6$–C$_{14}$ alkyl group.

39. A method according to claim 37, wherein the cationic surfactant is cetyl dimethyl ammonium chloride.

40. A method according to claim 37, further comprising combining from about 0.01% to about 20% by weight based on the total weight of the composition of a nonionic surfactant.

41. A method according to claim 40, wherein the nonionic surfactant is selected from the group consisting essentially of polyethylene glycol esters, alkanolamides, alkoxylated alcohols or a mixture thereof.

42. A method according to claim 40, further comprising combining from about 0.01% to about 20% by weight based on the total weight of the composition of an auxiliary anionic surfactant.

43. A method according to claim 42, wherein the auxiliary anionic surfactant is selected from the group consisting essentially of alpha olefin sulfonates, alkyl sulfates, alkyl alkoxy sulfates or a mixture thereof.

44. A method according to claim 40, further comprising combining from about 0.01% to about 5% by weight based on the total weight of the composition of an inorganic salt.

45. A method according to claim 44, wherein the an inorganic salt is selected from the group consisting essentially of sodium chloride, ammonium chloride, magnesium chloride or a mixture thereof.

46. A method according to claim 37, wherein the composition when diluted to a concentration of about 0.1 percent by weight in water forms a clear aqueous solution substantially free of precipitates at 25° C.

47. A method according to claim 37, wherein the viscosity of the composition is from about 200 cps to about 30,000 cps, at 25° C.

48. A method according to claim 37, wherein the total concentration of combined cationic, anionic, and bridging surfactants is from about 4% to about 30% by weight based on the total weight of the composition.

49. A method of cleaning and/or conditioning hair or skin comprising
(a) optionally wetting the skin or hair;
(b) applying, to the skin or hair an effective cleaning and/or conditioning amount of a surfactant composition comprising
  i) from about 0.05% to about 5% by weight based on the total weight of the composition of a cationic surfactant which is a quaternary ammonium compound of the formula:

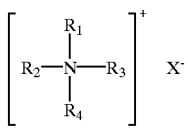

where
$R^1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and
an anionic surfactant comprising
a) from about 3% to about 22% by weight based on the total weight of the composition of an alpha sulfonated alkyl ester of the formula

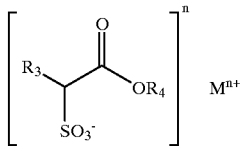

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and
b) from about 0.01% to about 11% by weight based on the total weight of the composition of a sulfonated fatty acid of the formula

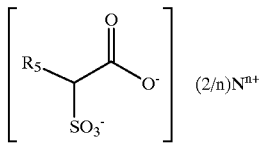

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and
wherein the weight ratio of a) to b) is from about 10:1 to about 0.5:1; and
iii) from about 0.01% to about 15% by weight based on the total weight of the composition a bridging surfactant selected from the group consisting of amine oxides, ethoxamides, and betaines or a mixture thereof; and
iv) water;
wherein the total concentration of combined cationic, anionic, and bridging surfactants is from about 3% to about 40% by weight based on the total weight of the composition; and
(c) optionally rising the surfactant composition from the skin or hair with water.

50. A method of cleaning and/or conditioning hair or skin comprising
(a) optionally wetting the skin or hair;
(b) applying to the skin or hair an effective cleaning and/or conditioning amount of a surfactant composition comprising
i) from about 0.05% to about 5% by weight based on the total weight of the composition of a cationic surfactant which is a quaternary ammonium compound of the formula:

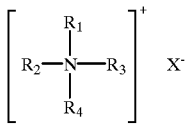

where
$R_1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate; and
ii) an anionic surfactant comprising
a) from about 3% to about 25% by weight based on the total weight of the composition of an alpha sulfonated alkyl ester of the formula

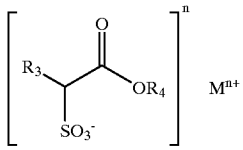

wherein $R_3$ is a $C_6$–$C_{22}$ hydrocarbyl group, an alkyl group, or combination thereof, $R_4$ is a straight or branched chain $C_1$–$C_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and
b) from about 0.01% to about 15% by weight based on the total weight of the composition of a sulfonated fatty acid of the formula

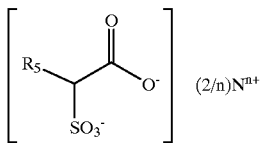

wherein $R_5$ is a $C_6$–$C_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and
wherein the weight ratio of a) to b) is from about 10:1 to about 0.5:1; and
iii) from about 0.01% to about 15% by weight based on the total weight of the composition a bridging surfactant selected from the group consisting of amine oxides, ethoxamides, and betaines or a mixture thereof; and iv) water;

wherein the total concentration of combined cationic, anionic, and bridging surfactants is from about 3% to about 40% by weight based on the total weight of the composition; and (c) optionally rising the surfactant composition from the skin or hair with water.

* * * * *